(12) United States Patent
Ghandi et al.

(10) Patent No.: US 11,497,701 B2
(45) Date of Patent: *Nov. 15, 2022

(54) MULTI-FUNCTIONAL ANTI-MICROBIAL POLYMERS AND COMPOSITIONS CONTAINING SAME

(71) Applicant: CHEMGREEN INNOVATION INC., Eden Mills (CA)

(72) Inventors: Khashayar Ghandi, Sackville (CA); Zahid Mahimwalla, Sackville (CA); Michael Kairiss, Killingsworth, CT (US); Yang Tan, Sackville (CA); Felix Baerlocher, Sackville (CA)

(73) Assignee: CHEMGREEN INNOVATION INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/762,252

(22) PCT Filed: Sep. 22, 2016

(86) PCT No.: PCT/CA2016/051111
§ 371 (c)(1),
(2) Date: Mar. 22, 2018

(87) PCT Pub. No.: WO2017/049402
PCT Pub. Date: Mar. 30, 2017

(65) Prior Publication Data
US 2018/0271769 A1 Sep. 27, 2018

Related U.S. Application Data

(60) Provisional application No. 62/221,762, filed on Sep. 22, 2015.

(51) Int. Cl.
| A01N 37/44 | (2006.01) |
| A61P 1/00 | (2006.01) |
| A61K 8/81 | (2006.01) |
| A01N 39/00 | (2006.01) |
| A01N 33/12 | (2006.01) |
| A01N 41/12 | (2006.01) |
| A01N 57/34 | (2006.01) |
| A01N 43/40 | (2006.01) |
| A01N 25/10 | (2006.01) |
| A61L 2/00 | (2006.01) |
| A01N 37/10 | (2006.01) |
| A61Q 17/00 | (2006.01) |
| C08G 61/02 | (2006.01) |

(52) U.S. Cl.
CPC ............ *A61K 8/8158* (2013.01); *A01N 25/10* (2013.01); *A01N 33/12* (2013.01); *A01N 37/10* (2013.01); *A01N 39/00* (2013.01); *A01N 41/12* (2013.01); *A01N 43/40* (2013.01); *A01N 57/34* (2013.01); *A61L 2/0088* (2013.01); *A61Q 17/005* (2013.01); *C08G 61/02* (2013.01); *C08G 2261/124* (2013.01); *C08G 2261/143* (2013.01); *C08G 2261/1426* (2013.01); *C08G 2261/312* (2013.01); *C08G 2261/3327* (2013.01)

(58) Field of Classification Search
None
See application file for complete search history.

(56) References Cited

U.S. PATENT DOCUMENTS

2003/0064102 A1* 4/2003 Nakatsuka ............. A01N 25/10
424/486

FOREIGN PATENT DOCUMENTS

| JP | 2002/265926 | 9/2002 | |
| WO | WO 2014/201544 | * 12/2014 | ............... A61K 8/81 |
| WO | WO2014/201544 | 12/2014 | |
| WO | WO-2014201544 A1 | * 12/2014 | |

OTHER PUBLICATIONS

Jizhen Ma, Jintao Zhang, Zhigang Xiong, Yu Yong and X. S. Zhao. Preparation, characterization and antibacterial properties of silver-modified graphene oxide. J. Mater. Chem., 21:3350-3352 (2011).
Shawn A. Messer; Daniel J. Diekema; * Richard J. Hollis, Linda B. Boyken, Shailesh Tendolkar,Jennifer Kroeger, and Michael A. Pfaller*. Evaluation of Disk Diffusion and Etest Compared to Broth Microdilution for Antifungal Susceptibility Testing of Posaconazole against Clinical Isolates of Filamentous Fungi. Journal of Clinical Microbiology 45(4):1322-1324, (2007).
Justin W. Hicks, Christian B. Kyle, Christopher M. Vogels, Susan L. Wheaton,Felix J. Baerlocher, Andreas Decken, and Stephen A. Westcott. Synthesis, Characterization, and Antifungal Activity of Boron-Containing Thiosemicarbazones. Chemistry & Biodiversity, 5:2415-2422, (2008).

* cited by examiner

Primary Examiner — Brian Gulledge
(74) Attorney, Agent, or Firm — Bereskin & Parr LLP/S.E.N.C.R.L, s.r.l.; Michael Fenwick

(57) ABSTRACT

The present disclosure relates to multi-functional anti-microbial polymers comprising a first monomer having a polymerizable cyclic aromatic moiety which forms part of the backbone of the polymer and a second monomer having an ethylenically unsaturated monomer having a double or triple bond and a quaternary ammonium or quaternary phosphonium moiety.

9 Claims, 11 Drawing Sheets

US 11,497,701 B2

MULTI-FUNCTIONAL ANTI-MICROBIAL POLYMERS AND COMPOSITIONS CONTAINING SAME

CROSS REFERENCE TO RELATED APPLICATIONS

This is a national stage application of PCT/CA2016/051111, filed Sep. 22, 2016, which claims priority from U.S. Provisional patent application Ser. No. 62/221,762, filed Sep. 22, 2015, all of which are incorporated herein by reference in their entirety.

FIELD

The present disclosure relates to multi-functional anti-microbial polymers and compositions containing the same.

INTRODUCTION

Dental resins, lotions, creams, hand sanitizers and other cosmetic formulations are generally a combination of several components working together to produce a desired functional and aesthetic effect. Such components include rheological modifiers, which thicken the formulation as needed, emulsifiers and surfactants which stabilize the suspension, as well as preservatives and biocides which disinfect or kill any microbial contamination. Other components, such as fragrances or moisturizers, may be included for the desired aesthetic or functional effect.

Formulators must therefore determine the appropriate combinations of these components such that they are not incompatible with the other ingredients of the formulation and perform as desired. For example, many rheological modifiers are anionic or neutral and can thus inactivate or be incompatible with common quaternary ammonium preservatives. Other rheological modifiers meanwhile, such as polysorbates and dextrans, are known to inactivate the antimicrobial efficacy of quaternary ammonium compounds (QACs). The inclusion of each of these components in a formulation must therefore be measured against the compatibility, activity, cost and performance of the other components with respect to each other, and the overall formulation performance. Other issues relate to the pH, and stability of the solution, whereby common components might change properties or become incompatible based on the solution pH, or become unstable over time, further necessitating additional experimentation and limiting the choice of ingredients used.

From an economic perspective this adds to the cost and complexity of the final product. They also require significant additional experimentation and development to test the compatibility of the various components in the formulation with respect to each other. Further, fossil fuel resources are still widely used as raw materials for the production of many of the above mentioned products resulting in products that are not environmentally friendly.

SUMMARY

The present disclosure relates to multi-functional anti-microbial polymers. In particular, the disclosure relates to anti-microbial polymers composed of polymerizable units of
i) a first monomer comprising a polymerizable cyclic aromatic moiety wherein the aromatic moiety is covalently incorporated into the polymer backbone through loss of aromaticity, and wherein the monomer further comprises an anti-microbial moiety which is a quaternary ammonium moiety, a quaternary phosphonium moiety or a sulfonium moiety;
ii) a second monomer comprising an ethylenically unsaturated double or triple bond and a quaternary ammonium moiety or a quaternary phosphonium moiety;
iii) optionally, at least one crosslinking monomer.

In one embodiment of the disclosure, the anti-microbial polymers are further crosslinked with a suitable crosslinking monomer to form crosslinked polymers.

In another embodiment, the anti-microbial polymers further comprise a monomer derived from a plant or fruit extract, wherein the monomer comprises a double bond or aromatic moiety. In one embodiment, the monomer derived from a plant or fruit extract is covalently incorporated into the polymer backbone through loss of aromaticity or double bond. In one embodiment, the polymers of the present disclosure have an E-factor that is close to zero.

In one embodiment, the anti-microbial polymers of the present disclosure are multi-functional in that they possess anti-microbial activity, and are also rheology modifiers, thickeners, and/or surfactant.

Also included in the present disclosure are compositions and/or formulations containing the multi-functional anti-microbial polymers. For example, the disclosure includes hand sanitizers, lotions, creams, sunscreens, comprising the multi-functional anti-microbial polymers.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DRAWINGS

The disclosure will now be described in greater detail with reference to the following drawings in which.

DESCRIPTION OF VARIOUS EMBODIMENTS

(I) DEFINITIONS

Figure 1:
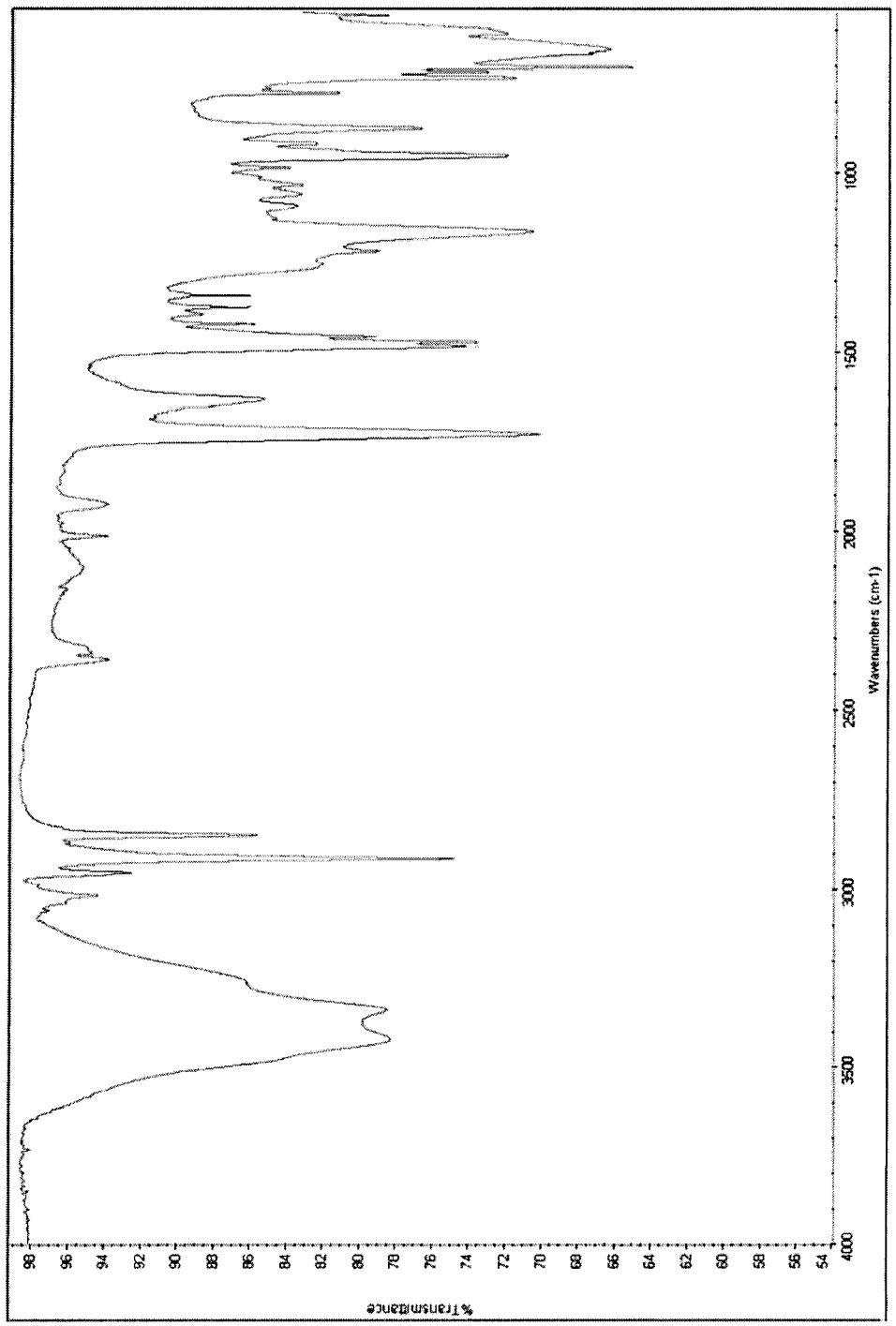
FIG. 1 is a Fourier Transform Infra-Red (FTIR) Spectrum of a polymer of the disclosure.

The term "anti-microbial polymer" as used herein refers to polymers of the present disclosure which kill, inhibit, and/or reduce microbial growth, for example, by inhibiting the proliferation or viability of a microbe which is undesirable and/or which disrupts a microbial cell. Microbes include bacteria, viruses, fungi, protozoa and the like.

The term "multi-functional" as used herein refers to the polymers of the disclosure possessing anti-microbial activity, as well as being rheology modifiers, thickeners and/or surfactants.

The term "polymerizable cyclic aromatic moiety" as used herein refers to a cyclic aromatic moiety of a monomer which can participate in a polymerization reaction. The aromatic moiety, for example, a benzene ring, directly participates in the polymerization reaction to form part of the backbone of the polymer that is prepared from the reaction.

The term "polymer backbone" as used herein refers to the covalently bonded chain of repeating monomer units that form the polymer. As would be understood, the polymer backbone may be covalently attached to terminal functional groups or pendant functionalized side chains spaced along the polymer backbone.

The term "anti-microbial moiety" as used herein refers to a moiety that possesses anti-microbial activity and which can therefore reduce kill, inhibit and/or reduce microbial growth. The anti-microbial activity of the prepared anti-microbial polymer exhibit similar or greater anti-microbial properties compared to the individual monomers which form the polymer. The term "anti-microbial moiety" also includes monomers which possess little or no anti-microbial activity, but exhibit anti-microbial properties upon polymerization to form the anti-microbial polymer.

The term "ethylenically unsaturated" as used herein refers to monomers having terminal, internal or pendant ethylenic unsaturation or any combination thereof and which can participate in a polymerization reaction. The ethylenic unsaturation may be a double or triple carbon-carbon bond.

The term "aromatic" as used herein with respect to the polymerizable cyclic moiety refers to a planar, cyclic or polycyclic, ring moiety having a delocalized π-electron system containing 4n+2π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "quarternary ammonium moiety" or "quarternary phosphonium moiety" as used herein refers to a moiety having four bonds to the nitrogen or phosphorous atom with a positive charge on the nitrogen or phosphorous in the "onium" state, i.e., "$R_4N^+$" or "quaternary nitrogen," wherein R is an organic substituent such as alkyl or aryl. The term "quaternary ammonium salt" or "quaternary phosphonium salt" as used herein refers to the association of the quaternary ammonium or phosphonium with a cation.

The term "quaternary aromatic ammonium or phosphonium" as used herein refers to a quaternary ammonium or phosphonium moiety as referred to herein, in which the monomer contains an aromatic moiety and a quaternary ammonium or phosphonium moiety, and in which the quaternary ammonium or phosphonium moiety does not form part of the aromatic ring. Examples of quaternary aromatic ammonium salts include, but are not limited to, benzalkonium chlorides (such as stearalkonium chloride, tetradecylammonium chloride), benzoxonium chloride, domiphen bromide, tibezonium chloride, benzethonium chloride, thonozium bromide, biphenium hydroxynaphthoate, etc. Examples of quaternary aromatic phosphonium salts include, but are not limited to, benzyltriphenylphosphonium chloride, benzyltriphenylphosphonium bromide, triphenyl-(3,4,5-trimethoxy-benzyl)-phosphonium bromide, benzyltriethylphosphonium chloride, benzyltributylphosphonium chloride, trimethylphenylphosphonium iodide, dimethyldiphenylphosphonium iodide, ethyl triphenyl phosphonium iodide, butyl triphenyl phosphonium bromide, methyl triphenyl phosphonium bromide.

The term "quaternary cyclic aromatic ammonium or phosphonium salt" as used herein refers to a quaternary ammonium moiety as referred to herein, in which the monomer contains an aromatic moiety and a quarternary ammonium moiety, in which the quarternary ammonium moiety forms part of the aromatic ring. Examples of quaternary cyclic aromatic ammonium salts include, but are not limited to, acriflavinium chloride, cetylpyrdinium chloride, chelerythrine, dequalinium, isometamidium chloride, ethidium bromide, diquat, MPP+ (1-methyl-4-phenylpyridinium) etc.

The term "acrylate" or "acrylamide" derivative as used herein refers to an alkyl ester or alkyl amide of acrylic acid, wherein the alkyl group further possesses a quarternary ammonium moiety. It is understood that the acrylic acid may be an unsubstituted or an alkyl (for example, $C_1$-$C_6$) substituted acrylic acid. Examples of the lower alkyl substituted acrylic acids are methacrylic acid, crotonic acid and the like.

The term "aryl" as used herein means a monocyclic, bicyclic or tricyclic aromatic ring system containing, depending on the number of atoms in the rings, for example from 6 to 14 carbon atoms, and at least 1 aromatic ring and includes phenyl, naphthyl, anthracenyl, 1,2-dihydronaphthyl, 1,2,3,4-tetrahydronaphthyl, fluorenyl, indanyl, indenyl and the like.

The term "heteroaryl" or "heteroaromatic" as used herein means a monocyclic, bicyclic or tricyclic ring system containing one or two aromatic rings, and from 5 to 14 atoms, optionally 5 or 6 atoms, of which, unless otherwise specified, one, two, three, four or five are a heteromoiety independently selected from N, NH, $NC_{1-6}$ alkyl, O and S and includes thienyl, furyl, pyrrolyl, pyrididyl, indolyl, quinolyl, isoquinolyl, tetrahydroquinolyl, benzofuryl, benzothienyl and the like.

The term "$(C_1$-$C_p)$_alkyl" as used herein means straight and/or branched chain, saturated alkyl radicals containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical.

The term "$(C_2$-$C_p)$alkenyl" as used herein means straight or branched chain, unsaturated alkyl groups containing from two to p carbon atoms and one to three double bonds, and includes (depending on the identity of p) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable p is an integer representing the largest number of carbon atoms in the alkenyl radical.

The term "$(C_2$-$C_p)$alkynyl" as used herein means straight and/or branched chain, unsaturated alkyl groups containing from one to n carbon atoms and one or more, suitably one to three, triple bonds, and includes (depending on the identity of p) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl4-methylpent-2-ynyl, 1-hexynyl and the like, where the variable n is an integer representing the largest number of carbon atoms in the alkynyl group.

The term "alkoxy" as used herein, alone or in combination, refers to an alkyl ether radical, —O-alkyl, wherein the alkyl group may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "counteranion" as used herein refers to a negatively charged species consisting of a single element, or a negatively charged species consisting of a group of elements connected by ionic and/or covalent bonds. Examples of suitable counteranions include, but are not limited to, the halides, for example chloro or bromo.

The suffix "ene" added on to any of the above groups means that the group is divalent, i.e. inserted between two other groups.

The term "halo" or "halogen" as used herein means halogen and includes chloro, fluoro, bromo and iodo.

The term "crosslinking monomer" as used herein refers to a compound which forms bonds (or "crosslinks") between two or more polymer chains (inter-crosslinking) or within a polymer chain itself (intra-crosslinking).

The term "a" as used herein is intended to mean "one or more" or "at least one", except where it is clear from the text that it means one. For example, the phrase "a first monomer" as used herein means that the polymer may contain one, or more than one, first monomers.

(II) DETAILED DESCRIPTION

The present disclosure relates to multi-functional anti-microbial polymers which, when brought into contact with the polymer, kill, inhibit and/or reduce microbial growth, or prevent the growth of microbes, including bacteria, fungi, viruses, protozoa, etc. In addition, the anti-microbial polymers are multi-functional, and when part of a composition or formulation, are also rheology modifiers, thickeners, surfactants, etc. Accordingly, compositions and formulations comprising the multi-functional anti-microbial polymers require less components than typical compositions known in the prior art.

The present disclosure relates to multi-functional anti-microbial polymers. The polymers of the present disclosure are prepared from monomers comprising a polymerizable cyclic aromatic moiety and an anti-microbial moiety, in which the aromatic moiety forms part of the polymer backbone, and an ethylenically unsaturated monomer comprising a double or triple bond. Such monomers may have anti-microbial properties as the monomers themselves, or become anti-microbial after polymerization, such that the anti-microbial polymer has similar or greater anti-microbial properties than the monomers alone.

In one embodiment, the present disclosure includes multi-functional anti-microbial polymers composed of polymerizable units of
  ii) a first monomer comprising a polymerizable cyclic aromatic moiety wherein the aromatic moiety is covalently incorporated into the polymer backbone through loss of aromaticity, and wherein the monomer further comprises an anti-microbial moiety which is a quaternary ammonium moiety, a quaternary phosphonium moiety or a sulfonium moiety;
  ii) a second monomer comprising an ethylenically unsaturated double or triple bond and a quaternary ammonium moiety or a quaternary phosphonium moiety; and
  iii) optionally, a crosslinking monomer.

In another embodiment, the anti-microbial polymers further comprise a monomer derived from a plant or fruit extract, wherein the monomer comprises a double bond or aromatic moiety. In one embodiment, the monomer derived from a plant or fruit extract is covalently incorporated into the polymer backbone through loss of aromaticity or double bond.

In one embodiment, the anti-microbial moiety of the first monomer and the quaternary ammonium moiety of the second monomer contribute to the multi-functional ability of the polymers to act as rheology modifiers, thickeners, emulsifier, surfactant etc.

In one embodiment, the first monomer comprises a radically polymerizable cyclic aromatic moiety. In one embodiment, the aromatic polymerizable cyclic moiety of the first monomer is unactivated.

In another embodiment, the anti-microbial moiety of the first monomer comprises a quaternary ammonium moiety or a quaternary phosphonium moiety. In one embodiment, the first monomer comprises a quaternary aromatic ammonium or phosphonium salt, or a quaternary cyclic aromatic ammonium or phosphonium salt.

In another embodiment of the disclosure, the first monomer is a quaternary aromatic ammonium, phosphonium or sulfonium salt of the formula

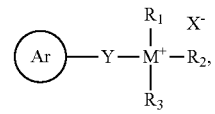

wherein
Ar is optionally substituted $(C_6-C_{14})$-aryl or optionally substituted $(C_5-C_{14})$-heteroaryl, Y is absent, $(C_1-C_{10})$-alkylene, $(C_2-C_{10})$-alkenylene, or $(C_2-C_{10})$-alkynylene, wherein 1 or 2 carbon atoms are optionally replaced with N, S or O;
$R_1$, $R_2$ and $R_3$ are independently or simultaneously optionally substituted H, $(C_1-C_{24})$-alkyl, $(C_2-C_{24})$-alkenyl, $(C_2-C_{24})$-alkynyl, $(C_6-C_{14})$-aryl, $(C_5-C_{14})$-heteroaryl or $(C_1-C_{10})$-alkylene-$(C_6-C_{14})$-aryl,
wherein the optional substituents are chosen from one or more of halogen, hydroxyl, $(C_1-C_6)$-alkyl, $(C_1-C_6)$-alkoxy, thionyl, nitro, amino (—$NH_2$), $(C_6-C_{14})$-aryl or $(C_5-C_{14})$-heteroaryl,
M is nitrogen, phosphorous or sulfur, wherein when M is sulfur, one of $R_1$, $R_2$ and $R_3$ is absent, and
X is any suitable counteranion, such as halo, In one embodiment, the ring Ar is involved in the polymerization reaction through loss of aromaticity.

In another embodiment, Ar is phenyl, naphthyl, anthracenyl, 1,2-dihydronaphthyl, 1,2,3,4-tetrahydronaphthyl, fluorenyl, indanyl, indenyl, thienyl, furyl, pyrrolyl, pyrididyl, indolyl, quinolyl, isoquinolyl, tetrahydroquinolyl, benzofuryl, or benzothienyl, each of which is optionally substituted. In one embodiment, Ar is optionally substituted phenyl.

In another embodiment, Y is $(C_1-C_6)$-alkylene, $(C_2-C_6)$-alkenylene, or $(C_2-C_6)$-alkynylene, wherein 1 or 2 carbon atoms are optionally replaced with O, optionally (C$_1$-C$_6$)-alkylene, in which one of the carbon atoms is optionally replaced with O.

In a further embodiment, R$_1$, R$_2$ and R$_3$ are independently or simultaneously (C$_1$-C$_{24}$)-alkyl, (C$_2$-C$_{24}$)-alkenyl, (C$_2$-C$_{24}$)-alkynyl, or (C$_1$-C$_{10}$)-alkylene-(C$_6$-C$_{14}$)-aryl. In one embodiment, R$_1$, R$_2$ and R$_3$ are independently or simultaneously optionally (C$_1$-C$_{24}$)-alkyl, or (C$_1$-C$_{20}$)-alkyl. In one embodiment, R$_1$, R$_2$ and R$_3$ are independently or simultaneously (C$_1$-C$_6$)-alkylene-phenyl.

In one embodiment, the first monomer is a quaternary aromatic salt having the formula

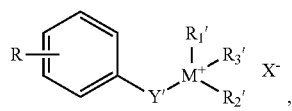

wherein
Y' is (C$_1$-C$_3$)-alkylene, wherein 1 carbon atom is optionally replaced with O;
R$_1$' and R$_2$' are independently or simultaneously (C$_1$-C$_4$)-alkyl optionally substituted with —OH;
R$_3$' is (C$_1$-C$_{24}$)-alkyl or (C$_1$-C$_{10}$)-alkylene-(C$_6$-C$_{14}$)-aryl, wherein 1 or 2 carbons of the (C$_1$-C$_{10}$)-alkylene group is optionally replaced with O, and the —(C$_6$-C$_{14}$)-aryl group is optionally substituted with (C$_1$-C$_{14}$)-alkyl; and
R is one or more optional substituents chosen from halogen, (C$_1$-C$_6$)-alkyl, thionyl, nitro, (C$_6$-C$_{14}$)-aryl or (C$_5$-C$_{14}$)-heteroaryl,
M is N, P or S, wherein when M is S, R$_1$' is absent, and
X is halo.

In one embodiment, the phenyl ring bonded to Y' is involved in the polymerization reaction through loss of aromaticity.

In one embodiment, Y is —O—CH$_2$CH$_2$— or CH$_2$.

In another embodiment, the first monomer is a quaternary aromatic ammonium salt which is

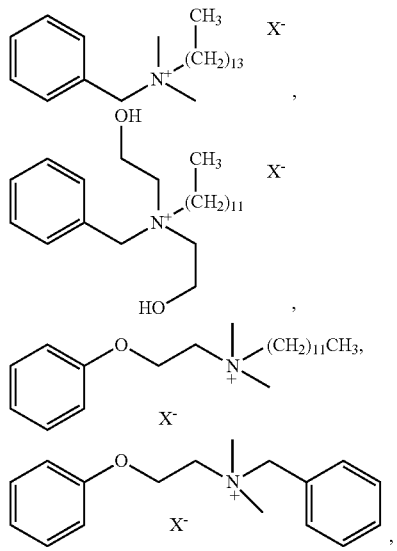

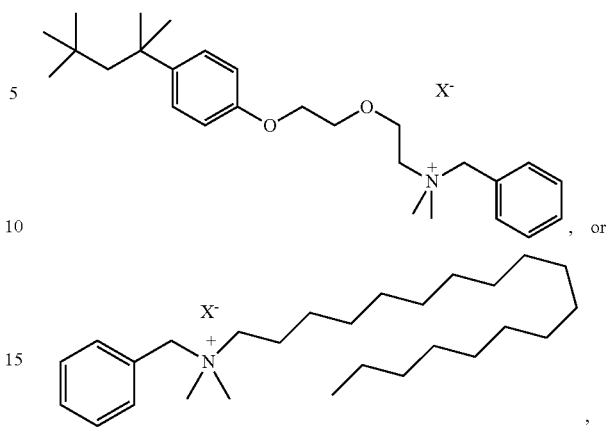

In another embodiment, the first monomer is a quaternary aromatic ammonium salt which is benzalkonium chloride, benzethonium chloride, or stearalkonium chloride. In one embodiment, benzalkonium chloride has the following chemical formula, wherein the phenyl ring is involved in the polymerization reaction through loss of aromaticity

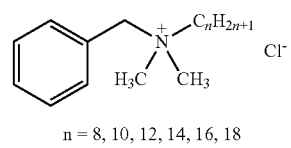

n = 8, 10, 12, 14, 16, 18

In another embodiment, the first monomer is a quaternary aromatic ammonium salt which is

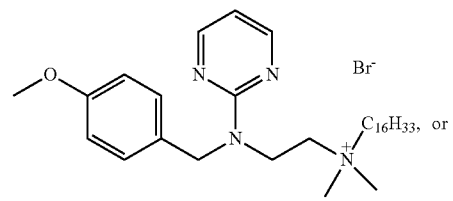

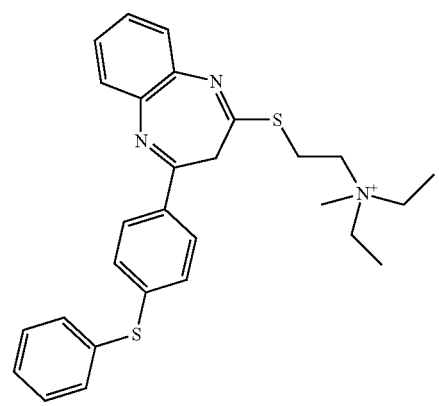

In another embodiment, the first monomer is a quaternary aromatic phosphonium salt which is

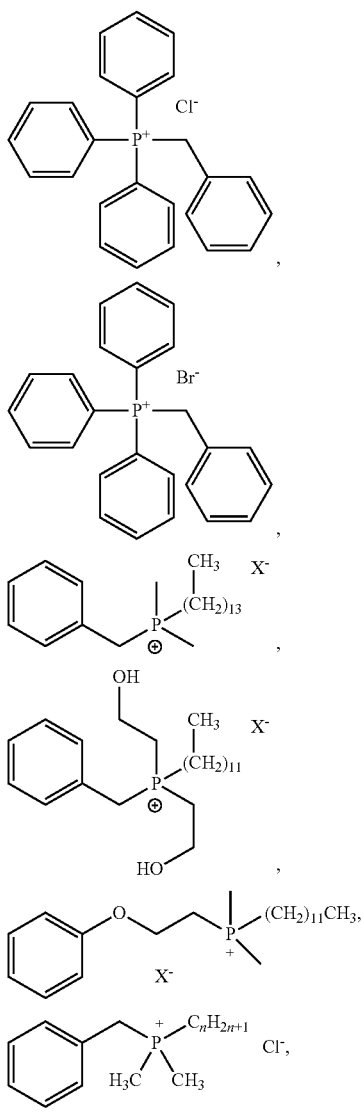
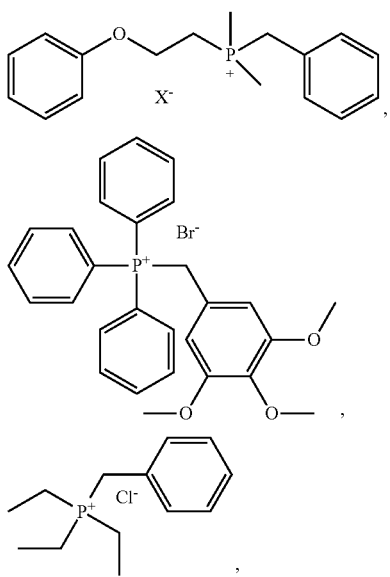
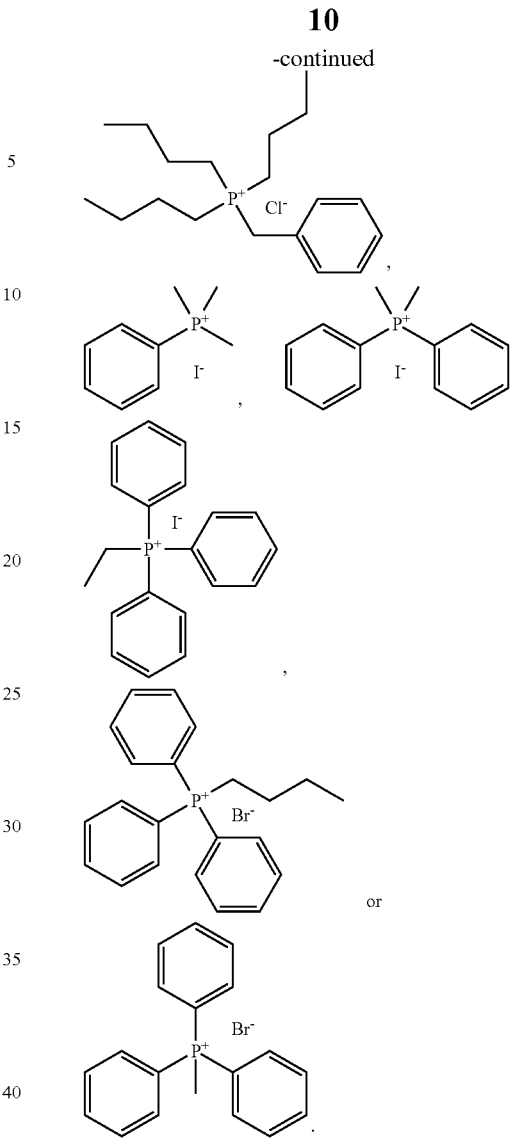
In another embodiment, the first monomer is a quaternary aromatic sulfonium salt which is
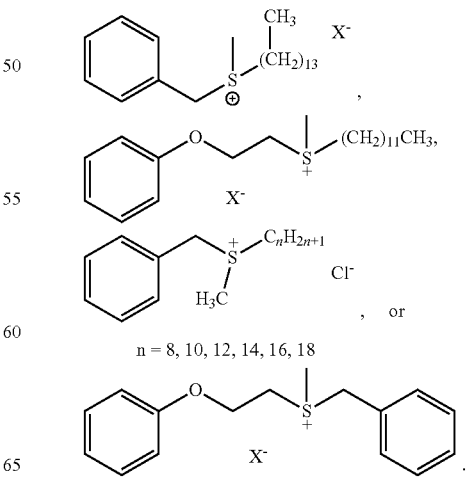

In another embodiment of the disclosure, the first monomer is a quaternary cyclic aromatic salt of the formula

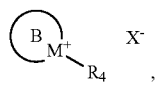

wherein
Ring B is an optionally substituted aromatic moiety containing from 5 to 18 carbon atoms, in which from 0 to 4 carbon atoms are replaced with a heteroatom selected from N, O and S,
$R_4$ is H, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl,
wherein the optional substituents are chosen from one or more of halogen, —OH, $(C_1-C_6)$-alkyl, $(C_1-C_6)$-alkoxy, thionyl, nitro, amino (—$NH_2$), $(C_6-C_{14})$-aryl, $(C_5-C_{14})$-heteroaryl, or two adjacent substituents are joined to form a methylene dioxy moiety,
M is N, P or S, wherein when M is S, $R_4$ is absent, and
X is any suitable counteranion, such as halo.

In one embodiment, Ring B is involved in the polymerization reaction through loss of aromaticity.

In one embodiment, Ring B is an optionally substituted aromatic moiety containing from 5 to 14 carbon atoms, in which from 0 to 2 carbon atoms are replaced with a heteroatom selected from N, O and S.

In one embodiment, $R_4$ is H or $(C_1-C_{24})$-alkyl, such as —$CH_3$, —$CH_2CH_3$ or —$C_{16}H_{33}$.

In another embodiment, the first monomer is a quaternary cyclic aromatic ammonium salt of the formula

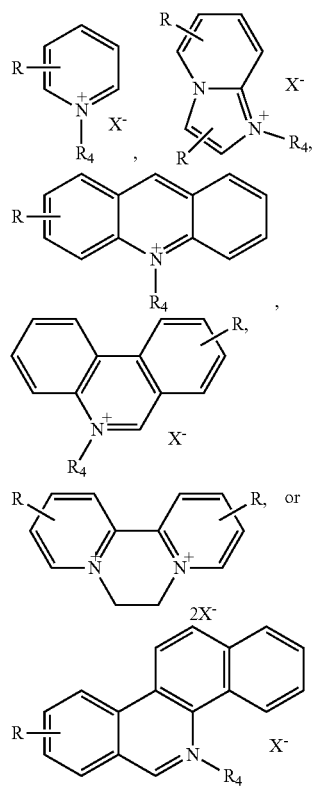

wherein
$R_4$ is H, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl,
R is one or more optional substituents chosen from halogen, —OH, $(C_1-C_6)$-alkyl, $(C_1-C_6)$-alkoxy, thionyl, nitro, amino (—$NH_2$), $(C_6-C_{14})$-aryl, $(C_5-C_{14})$-heteroaryl, or two adjacent substituents are joined to form a methylene dioxy moiety, and
X is any suitable counteranion, such as halo.

In one embodiment, $R_4$ is H or $(C_1-C_{24})$-alkyl, such as —$CH_3$, —$CH_2CH_3$ or —$C_{16}H_{33}$.

In one embodiment, the first monomer is a quaternary cyclic aromatic ammonium salt of the formula

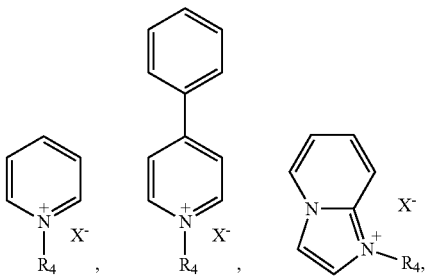

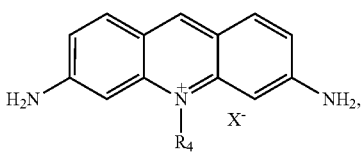

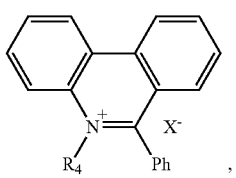

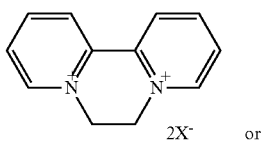

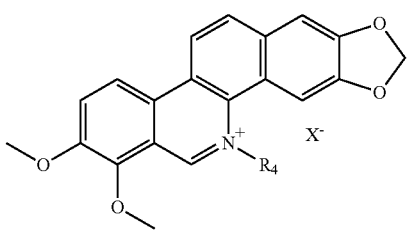

wherein
$R_4$ is H or $(C_1-C_{24})$-alkyl, and
X is any suitable counteranion, such as halo.

In another embodiment, the first monomer is a quaternary cyclic aromatic ammonium salt which is
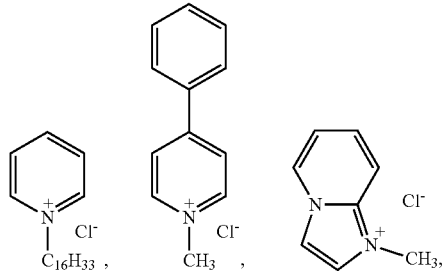
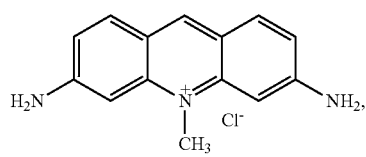
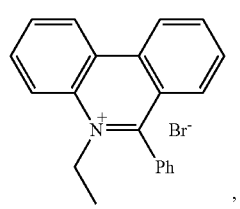
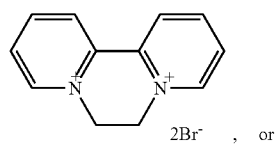
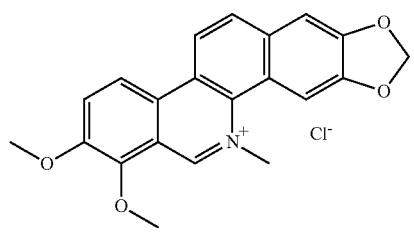
In one embodiment, the first monomer is a quaternary cyclic aromatic ammonium salt which is
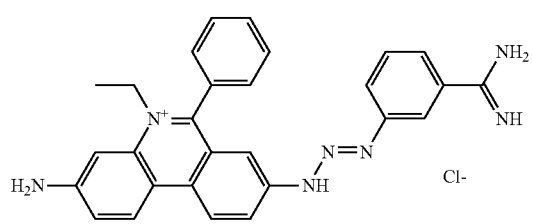
or
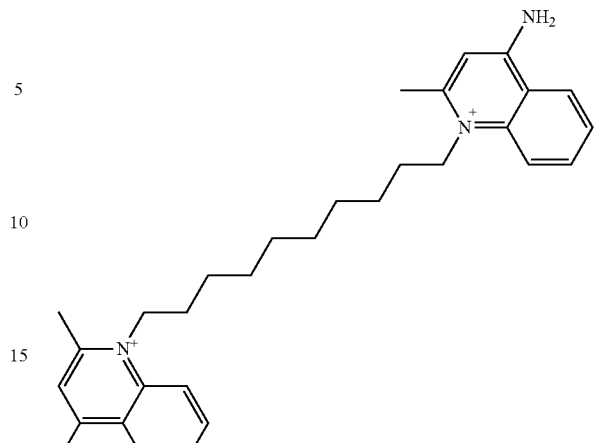
In another embodiment of the disclosure, the first monomer is
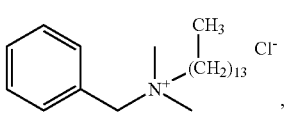
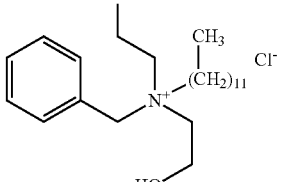
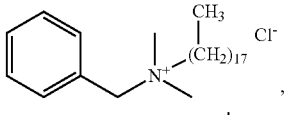
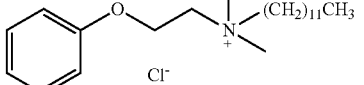
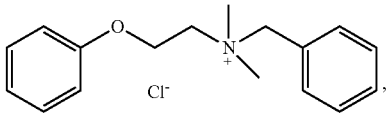
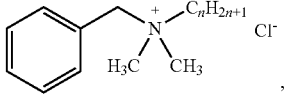
n = 8, 10, 12, 14, 16, 18
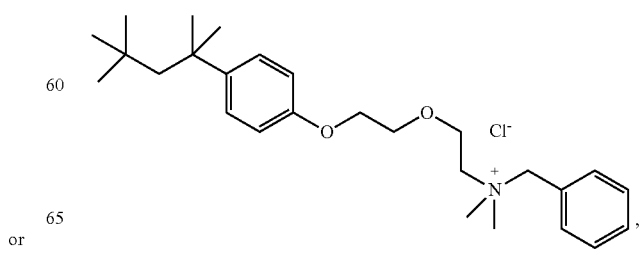

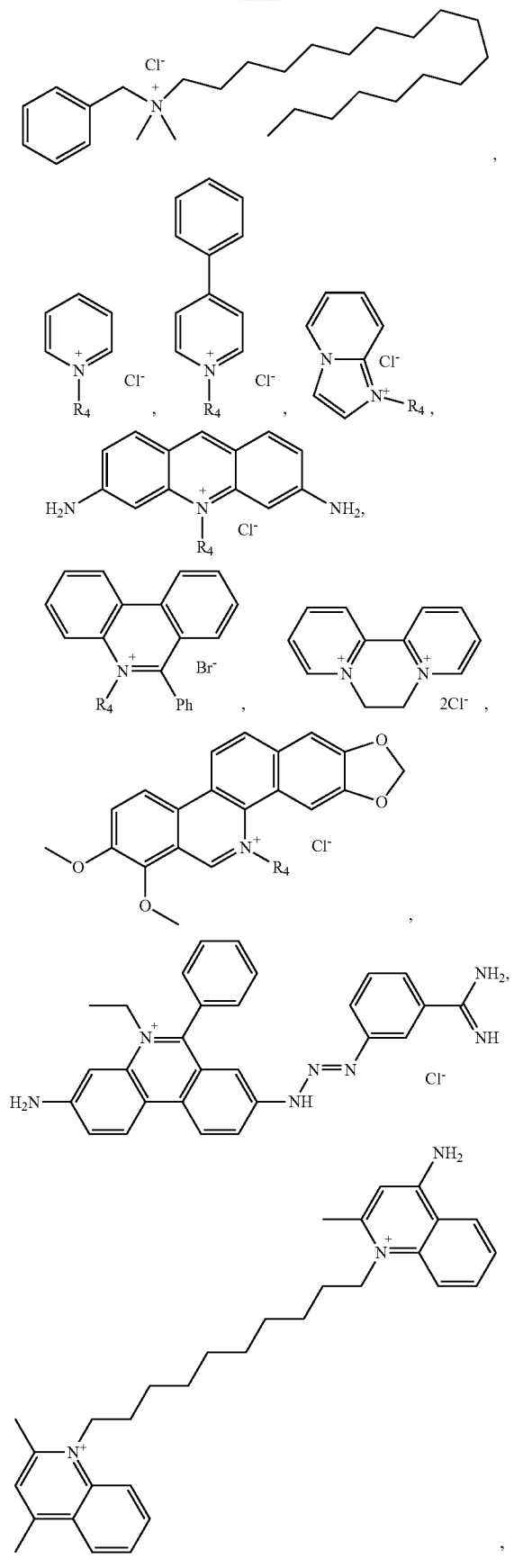

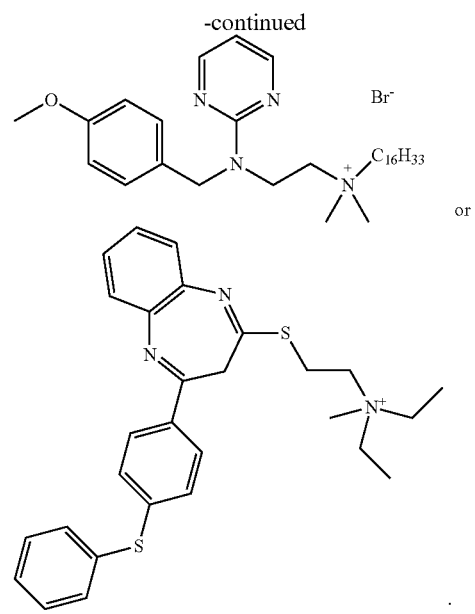

In one embodiment, the first monomer comprises a polymerizable cyclic aromatic moiety wherein the aromatic moiety is covalently incorporated into the polymer backbone through loss of aromaticity, and wherein the monomer is an antibiotic and has anti-microbial activity, such as ampicillin.

In one embodiment, the first monomer is present within the multi-functional anti-microbial polymer at a mole fraction of between 0.00001 to 0.99, or about 0.001 to about 0.90. In one embodiment, the mole fraction is between about 0.2 to about 0.8, or about 0.3 to about 0.7, or about 0.5.

In one embodiment, the multi-functional anti-microbial polymer is composed of one or more (for example, two or three) of any of the above-defined first monomers. For example, a multi-functional anti-microbial polymer may be prepared from benzalkonium chloride, benzethonium chloride, and stearalkonium chloride.

In another embodiment, the second monomer having an ethylenically unsaturated double or triple bond is any monomer having such unsaturation which participates in the polymerization reaction to form the multi-functional anti-microbial polymers of the present disclosure. Many monomers are known to those skilled in the art. In one embodiment, the second monomer possesses an ethylenically unsaturated double or triple bond and a quaternary ammonium moiety or a quaternary phosphonium moiety.

In one embodiment, the second monomer is an acrylate or acryalmide derivative having a quaternary ammonium or phosphonium moiety. In one embodiment, the acrylate derivative or acrylamide derivative has the formula

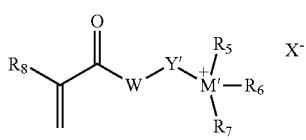

Y″ is absent, $(C_1$-$C_{10})$-alkylene, $(C_2$-$C_{10})$-alkenylene, or $(C_2$-$C_{10})$-alkynylene, wherein 1 or 2 carbon atoms are optionally replaced with N, S or O;

$R_5$, $R_6$ and $R_7$ are independently or simultaneously optionally substituted H, $(C_1$-$C_{24})$-alkyl, $(C_2$-$C_{24})$-alkenyl, or $(C_2$-$C_{24})$-alkynyl, $R_8$ is H or $(C_1-C_6)$-alkyl;
W is nitrogen or oxygen;
M' is nitrogen or phosphorous, and
X is any suitable counteranion, such as halo.

In another embodiment, Y" is absent, $(C_1-C_6)$-alkylene, $(C_2-C_6)$-alkenylene, or $(C_2-C_6)$-alkynylene, wherein 1 or 2 carbon atoms are optionally replaced with N, S or O. In another embodiment, Y" is $(C_1-C_6)$-alkylene, such as methylene, ethylene or propylene.

In another embodiment, $R_5$, $R_6$ and $R_7$ are independently or simultaneously optionally substituted $(C_1-C_{10})$-alkyl, $(C_2-C_{10})$-alkenyl, or $(C_2-C_{10})$-alkynyl. In another embodiment, $R_5$, $R_6$ and $R_7$ are independently or simultaneously optionally substituted $(C_1-C_6)$-alkyl, $(C_2-C_6)$-alkenyl, or $(C_2-C_6)$-alkynyl. In another embodiment, $R_5$, $R_6$ and $R_7$ are independently or simultaneously optionally substituted $(C_1-C_4)$-alkyl, such as methyl, ethyl or propyl.

In one embodiment, $R_8$ is methyl.
In another embodiment, M' is nitrogen.
In another embodiment, the acrylate derivative is

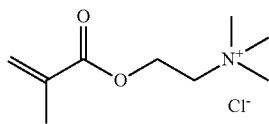

(methacryloxyethyltrimethyl ammonium chloride);

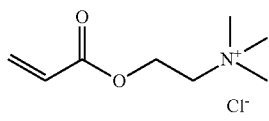

(acryloxyethyltrimethyl ammonium chloride) or

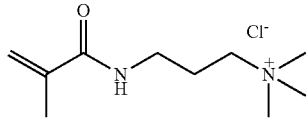

(methacrylamidopropyl trimethylammonium chloride).

Other unsaturated monomers having an ethylenically unsaturated double or triple bond include

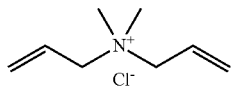

(diallyldimethylammonium chloride), or dimethylaminoethyl methacrylate.

In one embodiment, the second monomer is present within the anti-microbial polymer at a mole fraction of between 0.00001 to 0.99, or about 0.001 to about 0.90. In one embodiment, the mole fraction is between about 0.2 to about 0.9, or about 0.3 to about 0.8, or about 0.4 to about 0.7, or about 0.5.

In another embodiment, the multi-functional anti-microbial polymer is composed of one or more (for example, two or three) of any of the above-defined second monomers. For example, a multi-functional anti-microbial polymer may be prepared from methacryloxyethyltrimethyl ammonium chloride and acryloxyethyltrimethyl ammonium chloride.

In another embodiment of the disclosure, the multi-functional anti-microbial polymer comprises a polymer of the formula (Ia)

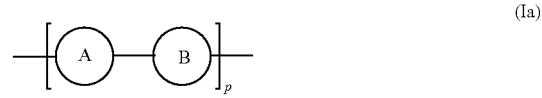

(Ia)

wherein
A is the first monomer,
B is the second monomer, and
p is any integer between 1 and 1,000,000.

In another embodiment of the disclosure, the multi-functional anti-microbial polymer comprises a polymer of the formula (Ib) wherein more than one mole equivalent of the second monomer is incorporated into the polymer

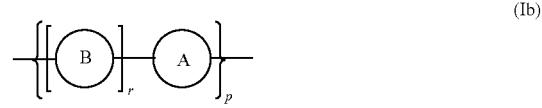

(Ib)

wherein
A is the first monomer,
B is the second monomer,
r is any integer between 1 and 10, and
p is any integer between 1 and 1,000,000.

In one embodiment, the properties of the multi-functional anti-microbial polymers of the present disclosure are modulated by controlling the variables p and r. For example, the rheological and anti-microbial properties of the polymer can be modulated by varying p. In another embodiment, p is any integer between 1-100,000, or 1-50,000, or 1-10,000, or 1-1,000, or 1-500, or 1-100, or 1-10 or 1-5.

In one embodiment, the anti-microbial polymer comprises a polymer of the formula (IA)

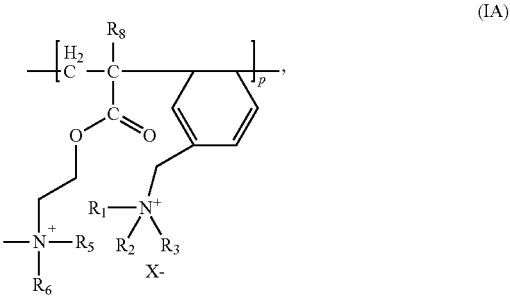

(IA)

wherein $R_1-R_8$ are as defined above,
X is any suitable counteranion, and
p is any integer between 1 and 1,000,000.

In one embodiment, $R_1$ and $R_2$ are methyl, and $R_3$ is $(C_8-C_{18})$-alkyl, optionally, $C_8$, $C_{10}$, $C_{12}$, $C_{14}$, $C_{16}$, or $C_{18}$, optionally, $C_{14}$; and $R_5$, $R_6$ and $R_7$ are methyl, and $R_8$ is H or methyl.

In one embodiment, the polymer of the formula (IA) is a polymer wherein the first monomer is benzalkonium chloride and the second monomer is [2-(Acryloyloxy)ethyl] trimethylammonium chloride, which has the following structure

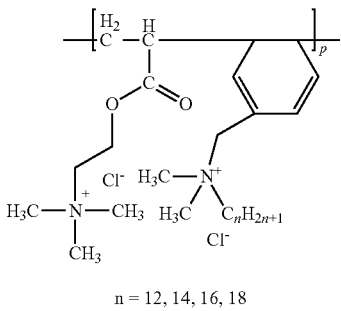

n = 12, 14, 16, 18

In another embodiment, p is any integer between 1-1,000,000, 1-100,000, or 1-50,000, or 1-10,000, or 1-1,000, or 1-500, or 1-100, or 1-10 or 1-5.

In another embodiment, the polymer of the formula (IA) is a polymer wherein the first monomer is benzalkonium chloride and the second monomer is methacryloxyethyltrimethyl ammonium chloride, which has the following structure

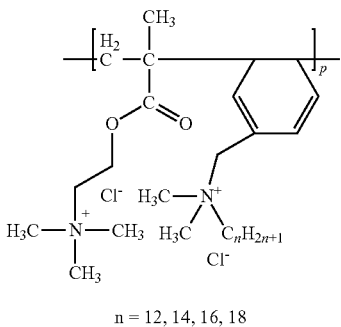

n = 12, 14, 16, 18

In another embodiment, p is any integer between 1-1,000,000, 1-100,000, or 1-50,000, or 1-10,000, or 1-1,000, or 1-500, or 1-100, or 1-10 or 1-5.

In another embodiment of the disclosure, the multi-functional anti-microbial polymers of the disclosure are crosslinked with a suitable crosslinking monomer. In one embodiment, the crosslinking monomer is any monomer which contains two or more polymerizable ethylenically unsaturated double or triple bonds. In one embodiment, the crosslinking monomer is allylsucrose, pentaerythritol allyl ether, vinyl ether, dimethacrylate, di- or tri-vinylbenzene, alicyclic dienes, ethylene glycol dimethacrylate, polyethylene glycol dimethyacrylate, penta- and tetra-acrylates and N-methylene-bis-acrylamide. In another embodiment, the crosslinking monomer is present in an amount of between 0.02% to 5%, optionally 0.1% to 5% by weight of the total monomer weight. In one embodiment, the identity and amount of crosslinking monomer is also used to control and tune the rheological and physical properties of the multi-functional anti-microbial polymers of the disclosure.

In another embodiment, the crosslinked polymers of the present disclosure form hydrogels having anti-microbial activity and also act as rheological modifiers.

In another embodiment, the anti-microbial polymers further comprise a monomer derived from a plant or fruit extract, wherein the monomer comprises a double bond or aromatic moiety. In one embodiment, the monomer derived from a plant or fruit extract is covalently incorporated into the polymer backbone through loss of aromaticity or double bond. In one embodiment, the plant or fruit extract is derived from sorbus decora, bistort, Laurus nobilis, Physalis alkekengi, pine leaves and barks, cedar leaves and barks, oak leaves and barks, fir leaves and barks, American beech leaves and barks, maple leaves and barks, yellow poplar leaves and barks, sycamore leaves and barks, Tulip Tree leaves and barks, sweet gum leaves and barks, leaves and barks and flowers of *Aster umbellatus*, leaves and barks and flowers of *Kalmia angustifolia*, leaves and barks and flowers of *Solidago Canadensis*, leaves and barks and flowers of *Aster acuminatus*, leaves and barks and fruits and flowers of *Corylus cornuta*, leaves and barks and fruits of *Prunus virginiana*.

In one embodiment, the plant or fruit extract comprises a tannin, terpenoid, alkaloid or combination thereof, wherein the tannin, terpenoid or alkaloid comprises a double bond or aromatic moiety which is incorporated into the polymer backbone. In one embodiment, the plant or fruit extract is from sorbus decora, bistort plant or other plant comprising a tannin, terpernoid, or alkaloid.

(IV) PROCESSES FOR PREPARATION OF THE DISCLOSURE

The polymers of the present disclosure are prepared using techniques known to those skilled in the art. In one embodiment, the polymers of the present disclosure are prepared using techniques as described in US publication no. 2012-0049101. In one embodiment, the anti-microbial polymers of the present disclosure are prepared in at least 95% yield, or about 98% yield, or about 99% yield, or 100% yield. In one embodiment, there are no by-products from the polymerization reaction to prepare the polymers of the present disclosure.

In one embodiment, the polymerization reaction is initiated by a free radical initiator. In another embodiment, the free radical initiator is an azo compound, a peroxide or a photo-catalytic initiator. In one embodiment, the azo compound is azobisisobutyronitrile (AIBN) or 1,1'-azobis(cyclohexanecarbonitrile). In one embodiment, the peroxy compound is di-tert-butyl peroxide, benzoyl peroxide or methyl ethyl ketone peroxide. In one embodiment, the polymerization processes for preparing the polymers of the disclosure are solvent-free with high yields of at least about 90%, or at least about 95%, or at least about 99%, or about 100 percent yield. In one embodiment, the E-factor of the processes of the disclosure is about zero.

In one embodiment, the polymerization reaction is initiated by a free radical initiator in a flow system drop by drop to control the reaction towards breaking aromaticity. In one embodiment, the polymerizable cyclic aromatic moiety is more reactive to polymerization and does not contain easily polymeriazble groups, such as vinyl groups, allyl groups.

In one embodiment, the polymerization reaction proceeds in the presence of an acid, for example, an organic acid or an inorganic acid, such as hydrochloric acid. In another embodiment, the acid is present in an amount between 0.01% and 20 wt % of total monomer weight. In one embodiment, the acid is hydrochloric acid, hydrobromic acid, hydroiodic acid, nitric acid, chloric acid, perchloric acid, sulfuric acid, citric acid or acetic acid.

In one embodiment, all of the reactants, including the monomers comprising a polymerizable cyclic aromatic moiety and the monomers having an ethylenically unsaturated double or triple bond, and optionally the radical initiators, form part of the anti-microbial polymers resulting in no waste products. In one embodiment, and without being bound by theory, a reaction mechanism is shown in Scheme 1:

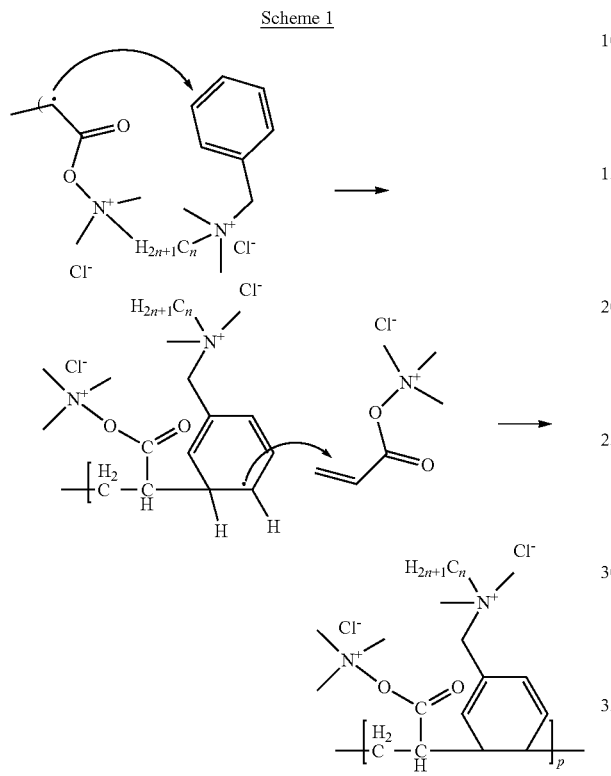

Scheme 1 n = 12, 14, 16

Scheme 1 demonstrates that the aromatic ring of the polymerizable cyclic aromatic moiety is involved in the polymerization reaction and forms part of the polymer backbone through loss of aromaticity. Scheme 2 shows a multi-functional anti-microbial polymer of the disclosure

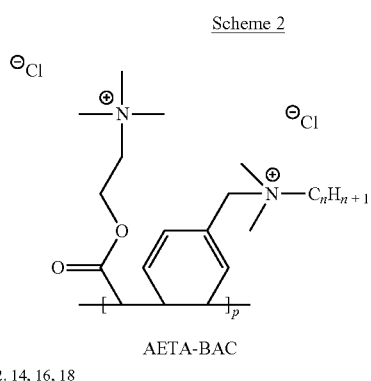

Scheme 2

AETA-BAC n = 12, 14, 16, 18

Scheme 3 shows chain termination of the polymerization reaction through hydrogen abstraction of a hydrogen from a polymerizable cyclic aromatic monomer.

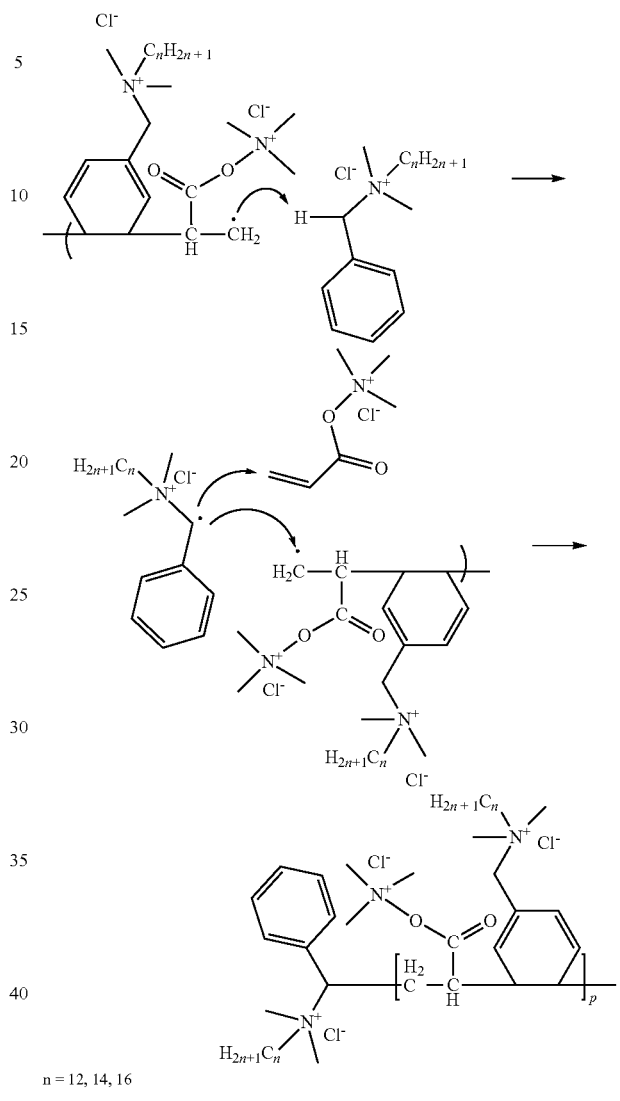

Scheme 3 n = 12, 14, 16

(IV) USES OF THE MULTI-FUNCTIONAL ANTI-MICROBIAL POLYMERS

The multi-functional anti-microbial polymers of the present disclosure are useful to prevent or inhibit the growth of microbes, such as bacteria, fungi, viruses and protozoa. In another embodiment, the multi-functional anti-microbial polymers are useful in formulations, such as anti-microbial hand sanitizers, creams, lotions, sunscreens etc., as the polymers can also act as rheology modifiers, thickeners, surfactants etc. In one embodiment, for example, a hand sanitizing formulation comprises a multi-functional anti-microbial polymer of the present disclosure and water, and does not require other additives which affect the physical properties of the composition, such as rheological modifiers, emulsifiers, thickeners, foamers, surfactants etc. In one embodiment, the hand sanitizer consists essentially of, or consists of, a multi-functional anti-microbial polymer and water. Scents, essential oils, and/or moisturizers (such as aloe vera) may be added to the formulation, but such components do not affect the physical properties (i.e. viscosity) of the formulation.

The multi-functional anti-microbial polymers of the present disclosure may also be formulated into lotions, creams, sunscreens, ointments, gels, or any other pharmaceutical or dermatological formulation, for which anti-microbial activity is desired. Due to the multi-functional properties of the polymers of the present disclosure, the lotion, cream, sunscreen, etc. formulations do not require additional components to modulate the rheological properties of the formulation.

In one embodiment therefore, there is also included a use of a multi-functional anti-microbial polymer of the present disclosure as a rheology modifier.

In another embodiment, the multi-functional anti-microbial polymers of the present disclosure are suitable for use in a disinfectant or cleaning composition, or a cosmetic, dermatological or pharmaceutical preparation providing anti-microbial activity, as well as acting as a rheology modifier, thickener, emulsifier, surfactant etc., as required in the particular composition.

The disclosure also includes a disinfectant composition comprising a multi-functional anti-microbial polymer of the disclosure, wherein the amount of multi-functional anti-micrboial polymer is between 0.01% and 70% by weight of the final composition, or about 0.01% and 10%.

The disclosure further includes chemical compositions comprising a multi-functional anti-microbial polymer of the disclosure, where in the chemical composition is a pharmaceutical composition, cosmetic composition, personal care composition, cleansing composition, biocidal composition, industrial composition, oilfield, agricultural or pesticide composition. In one embodiment, the cosmetic composition is personal care, household, or cleaning composition. In another embodiment, the personal care composition is a skin lotion, crème, ointment, or salve, moisturizer, deodorant, tanning agent, sun block, sunscreen, nail polish, make-up remover, nail polish remover, shampoo, rinse-off conditioner, leave-on conditioner, hair styling gel, hair mousse, hair spray or mascara. In another embodiment, the cleansing composition is a liquid, gel, or foaming antimicrobial skin sanitizer that is optionally rinse less. In another embodiment, the polymers of the disclosure are used as dental resins for filling cavities, filling gaps in teeth.

In another embodiment, the present disclosure includes a skin sanitizer comprising
(a) approximately 0.01 wt. % to 15 wt. % of a multi-functional anti-microbial polymer of the disclosure,
(b) approximately 50 wt. % to 99.99 wt. % water,
(c) optionally 0.01 wt. % to 30 wt. % emollient,
(d) optionally 0.5 wt. % to 20 wt. % emulsifier,
(e) optionally 0.01 wt. % to 3 wt. % fragrance,
(f) optionally 0.1 wt. % to 10 wt. % humectants or moisturizers, In one embodiment, the skin sanitizer can be applied to gloves or hands and the solution will dry after application.

In another embodiment, the present disclosure includes a disinfectant or cleaning composition, wherein the composition is a liquid or foam, rinseable handwash or soap, comprising
(a) approximately 0.01 wt. % to 15 wt. % of a multi-functional anti-microbial polymer of the disclosure,
(b) approximately 50 wt. % to 99 wt. % water,
(c) approximately 1 wt. % to 10 wt. % non-ionic or cationic surfactant,
(d) optionally 0.1 wt. % to 10 wt. % humectants or moisturizers,
(e) optionally 0.01 wt. % to 3 wt. % fragrance,
(f) optionally 0.01 wt. % to 30 wt. % emollient,
(g) optionally 0.5 wt. % to 20 wt. % emulsifier.

In another embodiment, the disinfectant or cleaning composition is a hard surface cleaner, heavy duty cleaner or detergent in the pH range of 1 to 5 or 9 to 12, comprising:
(a) approximately 0.01 wt. % to 15 wt. % a multi-functional anti-microbial polymer of the disclosure,
(b) approximately 50 wt. % to 95.99 wt. % water,
(c) approximately 4 wt. % to 30 wt. % of pH adjuster
(e) optionally 0.01 wt. % to 3 wt. % fragrance, In another embodiment, the personal care composition comprises
(a) approximately 0.01 wt. % to 15 wt. % multi-functional anti-microbial polymer of the disclosure,
(b) approximately 40 wt. % to 99.99 wt. % water,
(c) optionally 0.01 wt. % to 30 wt. % emollient,
(d) optionally 0.5 wt. % to 20 wt. % emulsifier,
(e) optionally 0.01 wt. % to 3 wt. % fragrance,
(f) optionally 0.1 wt. % to 10 wt. % humectants or moisturizers,
(h) optionally 1 wt. % to 10 wt. % pH adjuster.

In another embodiment, the the emollient is selected from the group consisting of polysiloxanes, polyethers, polyesters, hydrocarbons with carbon numbers most above 20, polyols, natural oils, vegetable oils and combinations thereof. In one embodiment, the emollient is selected from the group consisting of dimethicone, amodimethicone, petroleum jelly, oils based on petrolatum, esters of propylene glycol, lanolin and its derivatives, glycerin, glycerol, derivatives of caprylic acid, C12-C15 alkyl benzoate, isopropyl isostearate, diisostearyl fumarate, diisostearyl malate, butyrospermum parkii (Shea) butter, mineral oils, almond oil, avocado oil, coconut oil, grapeseed oil, jojoba oil, sunflower oil, alkoxylated carboxylic acids, isostearyl hydrostearate, cetyl palmitate and combinations thereof.

In one embodiment, the emulsifier is selected from the group consisting of fatty alcohols, non-ionic polyoxyethylene ethers, polyethylene glycol, glucuronic acids, triglycerides and combinations thereof. In another embodiment, the emulsifier is selected from the group consisting of cetearyl alcohol, stearyl alcohol, cetyl alcohol, esters of glycerin or stearic acid, esters of oleic acid, glycol stearate, benzoates, glucuronic and galacturonic acids, gum Arabic, xanthan gum, guar gum, esters of polyethylene glycol, propylene glycol, sorbitan oleate, triglycerol esters, sodium borate and its derivatives, glycerin, glycerol polyethylene glycol stearate, emulsifying wax, ceteareth-20, and combinations thereof.

In another embodiment, the humectants or moisturizer is selected from the group consisting of protein extracts, natural polysaccharides, polyols and combinations thereof. In another embodiment, the humectants or moisturizer is selected from the group consisting of saccharide isomerate, citric acid, algae extract, hyaluronate gel, aloe vera extract, concentrate or powder, glycerin, glycerol, ceramide, propylene glycol, polyethylene glycol, petrolatum and petrolatum derivatives, lanolin, dimethicone, dimethicone polyethylene glycol derivatives, butylene glycol, panthenol, vegetable oil, mineral oil, sorbitol, D-glucitol, D-mannitol, urea and urea derivatives, tetrahexyldecyl ascorbate, dl-alpha tocopherol, cucumber extract, esters of polypropylene glycol, and combinations thereof.

In another embodiment, the non-ionic or cationic surfactant is selected from the group consisting of polysorbates, fatty alcohols, poloxamers, quarternary ammonium compounds, pH dependent primary, secondary and tertiary amines, and combinations thereof. In another embodiment, the non-ionic or cationic surfactant is selected from the group consisting of cetyl alcohol, stearyl alcohol, glyceryl laurate, decyl glucoside, lauryl glucoside, cocamide MEA, cocamide DEA, polysorbate, copolymers of polyethylene glycol and polypropylene glycol, dimethyldioctadecylammonium chloride, cetyl trimethylammonium chloride, cetrimonium bromide, benzethonium chloride, isoceteth-20, cetostearyl alcohol, octyl glucoside, Tween 20, Tween 60, Tween 80, and combinations thereof.

In another embodiment, the pH adjuster is glycolic acid, acetic acid, citric acid, gluconic acid, lactic acid, potassium hydroxide, ammonium hydroxide, sodium hydroxide, hydrochloric acid, triethanolamine, arginine, aminomethyl propanol, tromethamine, PEG-15 cocamine, tetrahydroxypropyl ethylenediamine, sulfuric acid, or a combination thereof.

In another embodiment of the disclosure, the anti-microbial polymers are suitable for use in wastewater treatment. For example, in one embodiment, the anti-microbial polymers are contacted with water in need of an anti-microbial treatment.

In another embodiment, the anti-microbial polymers of the present disclosure are useful as drilling fluid compositions in an oilfield. In one embodiment, the anti-microbial polymers, alone, or in combination with other common drilling fluid additives, are used in a drilling operation as a drilling fluid to recover oil from an oilwell or oilsands.

The operation of the disclosure is illustrated by the following representative examples. As is apparent to those skilled in the art, many of the details of the examples may be changed while still practicing the disclosure described herein.

(IV) EXAMPLES

Example 1

Preparation of a Multipurpose Anti-Microbial Polymer

Figure 3:
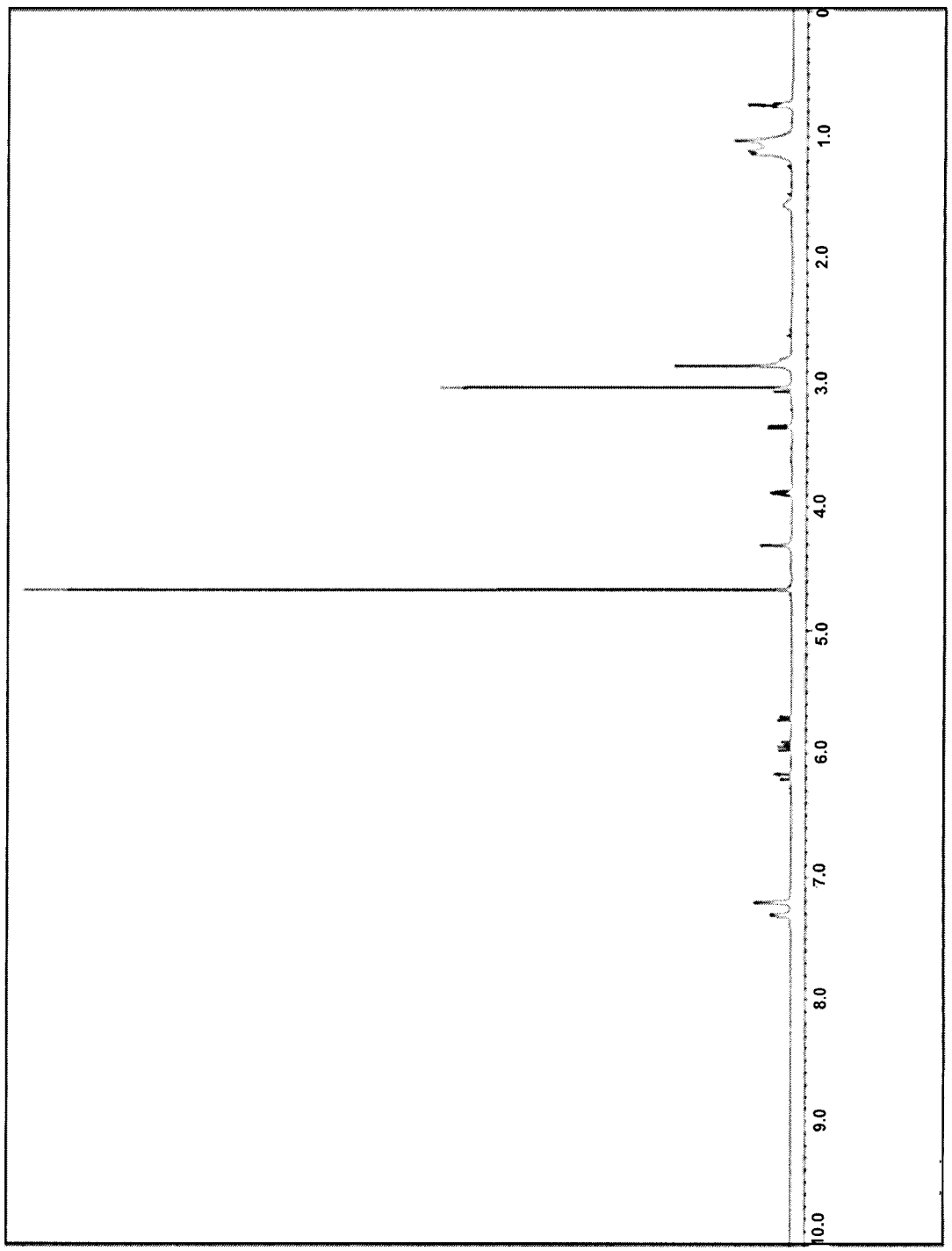
FIG. 3 is an $^1$H Nuclear Magnetic Resonance (NMR) spectrum of a polymer of the disclosure.
Figure 4:
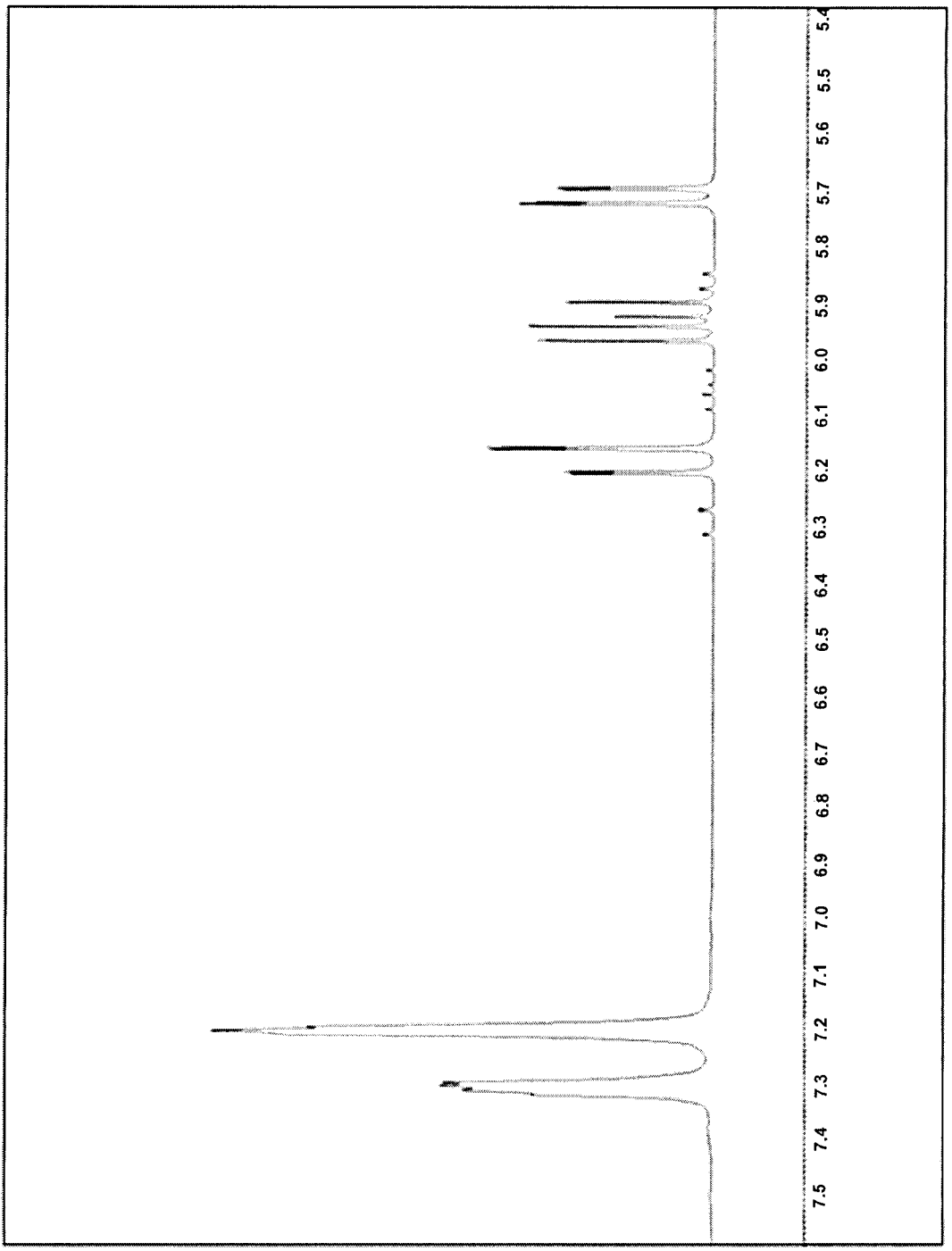
FIG. 4 is an $^1$H NMR spectrum of the aromatic region of a polymer of the disclosure.
Figure 5:
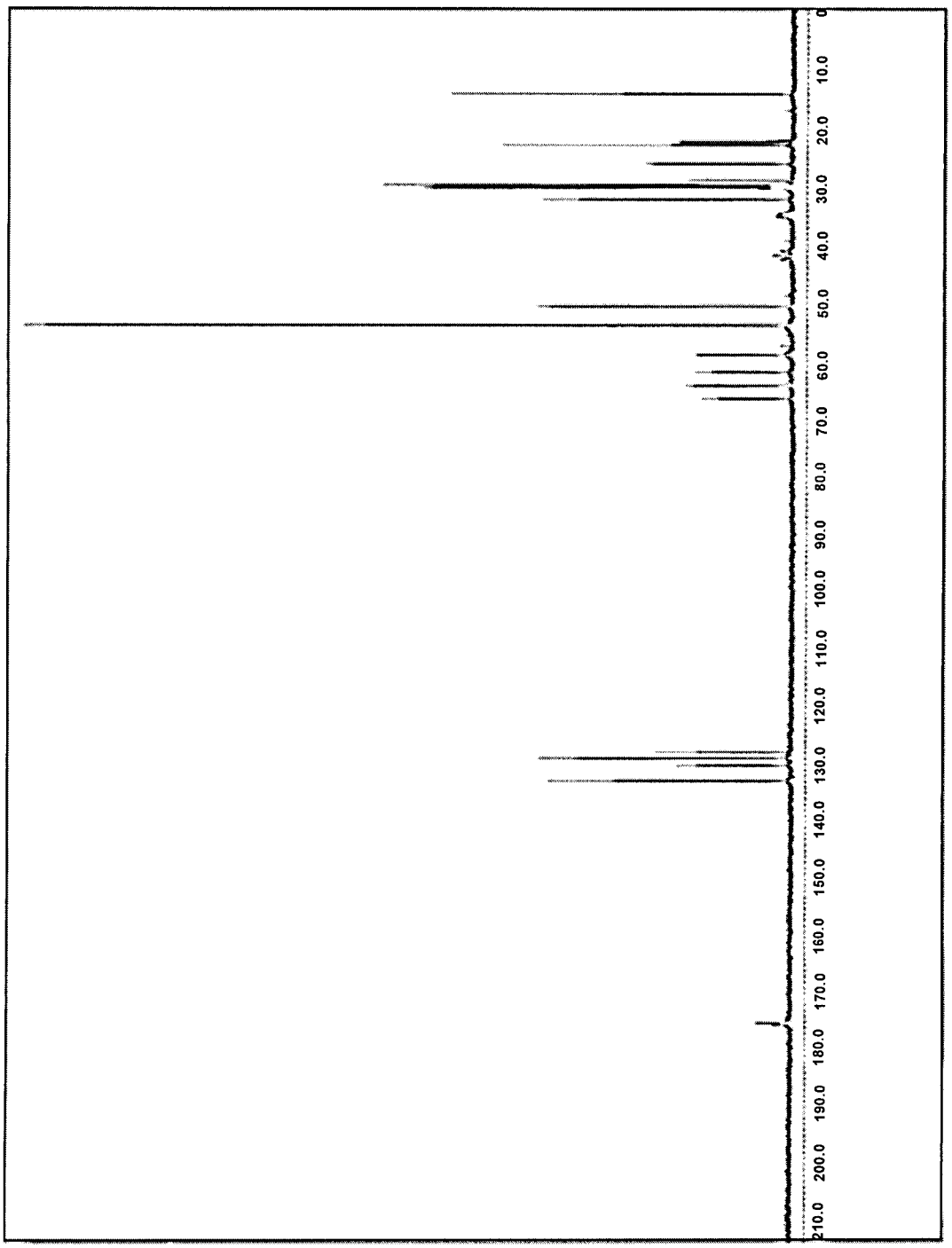
FIG. 5 is a $^{13}$C Nuclear Magnetic Resonance (NMR) spectrum of a polymer of the disclosure.
Figure 6:
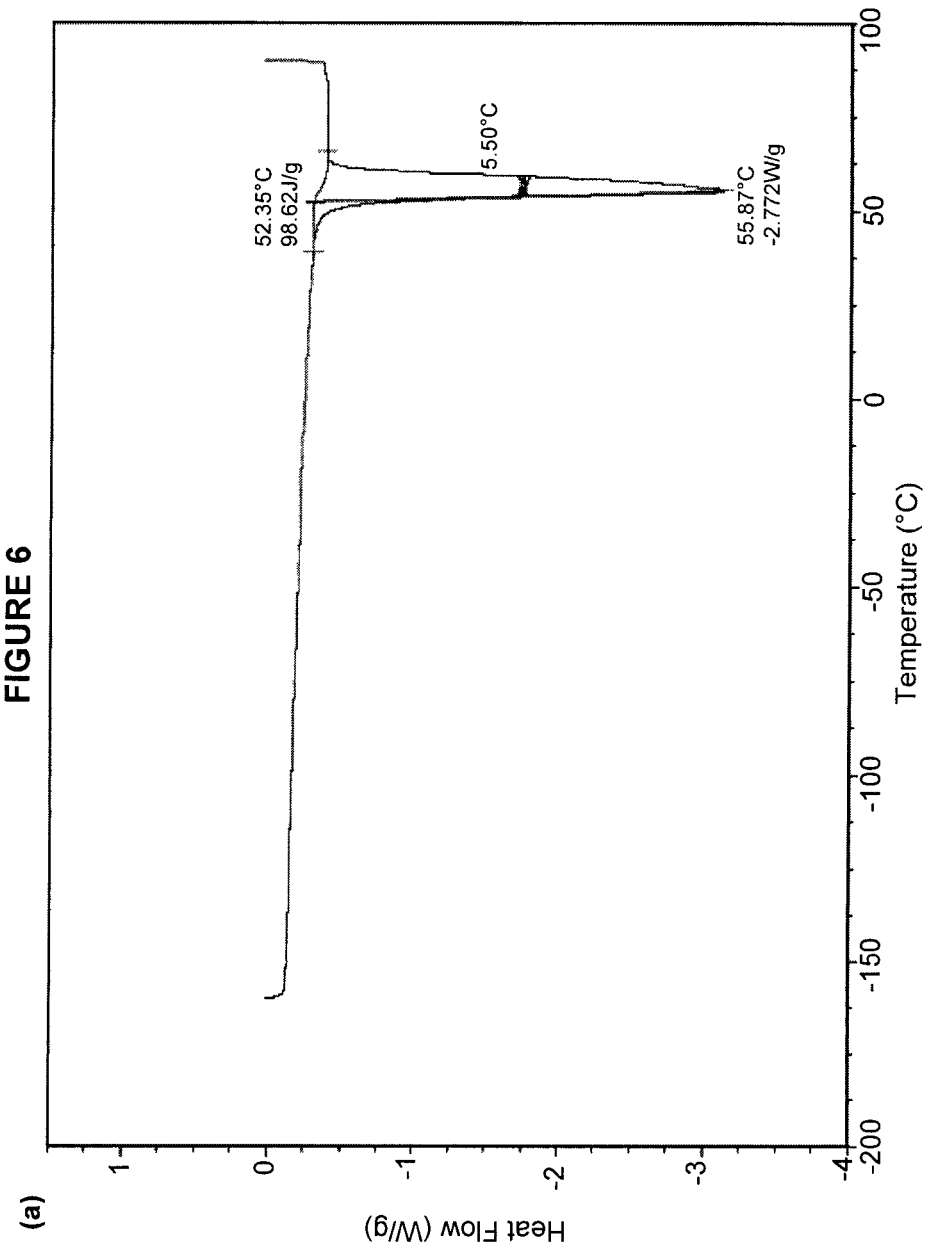
FIG. 6 is a Differential Scanning calorimetry (DSC) thermogram of a polymer of the disclosure.
Figure 6:
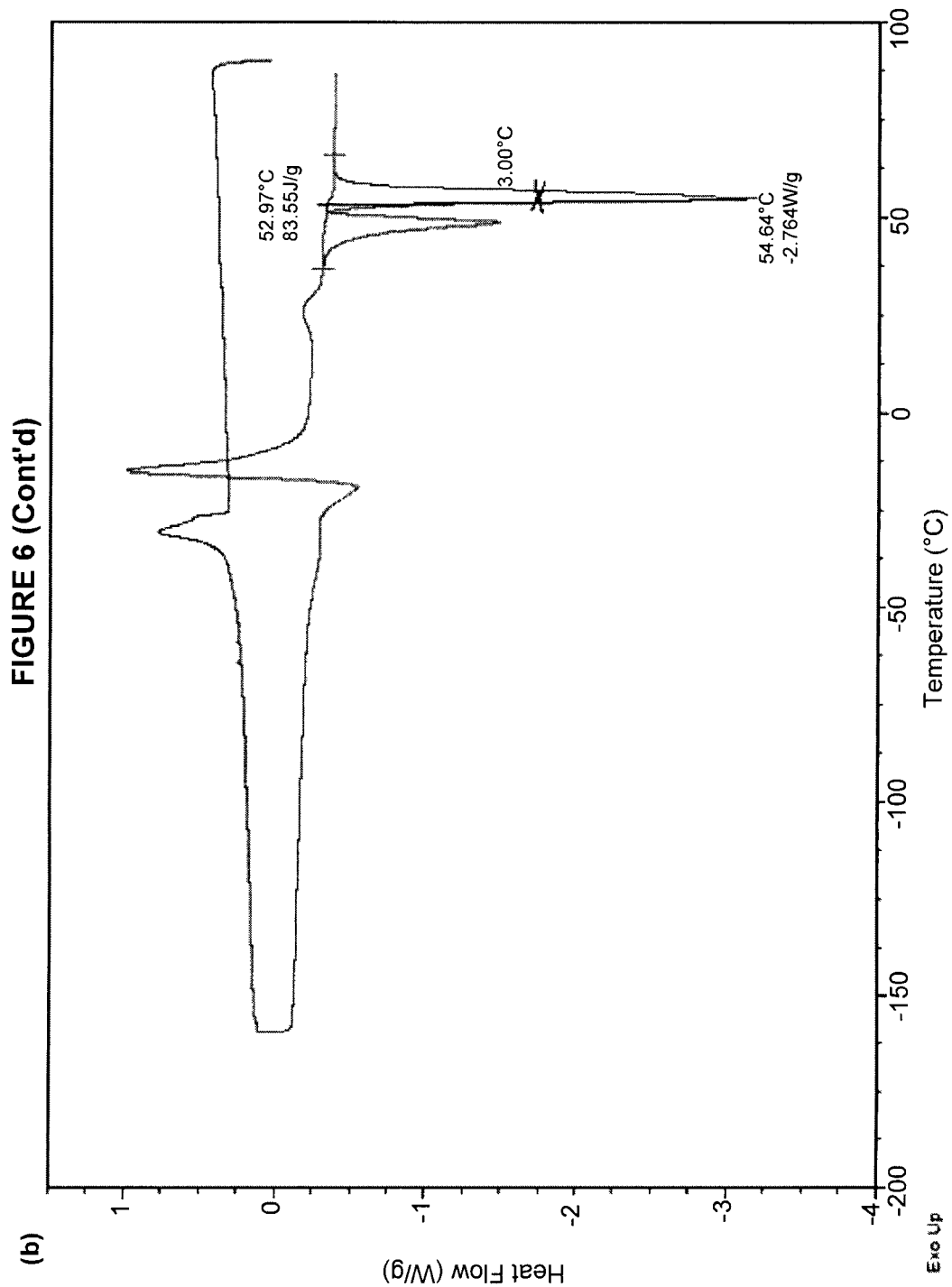
Figure 6:
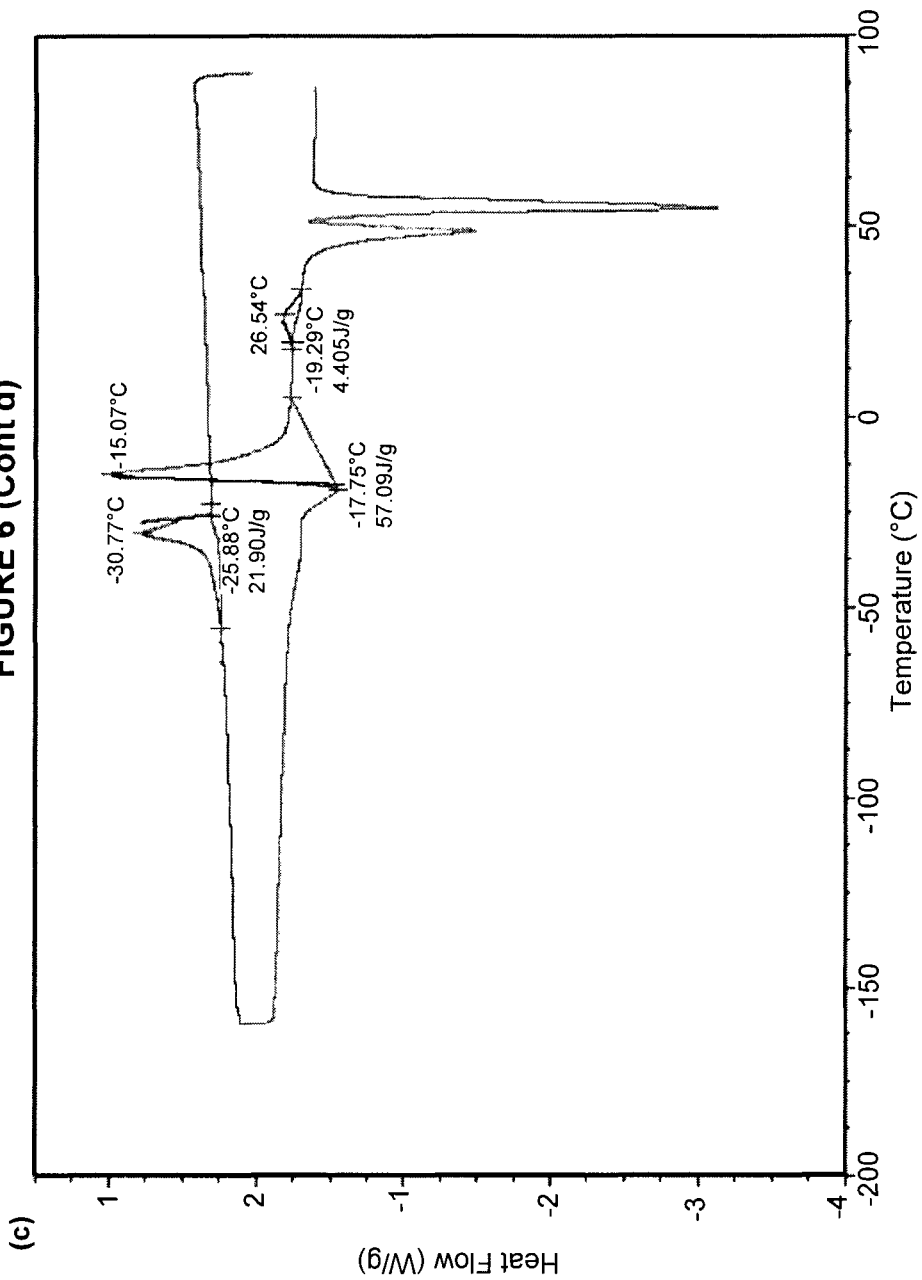
Figure 6:
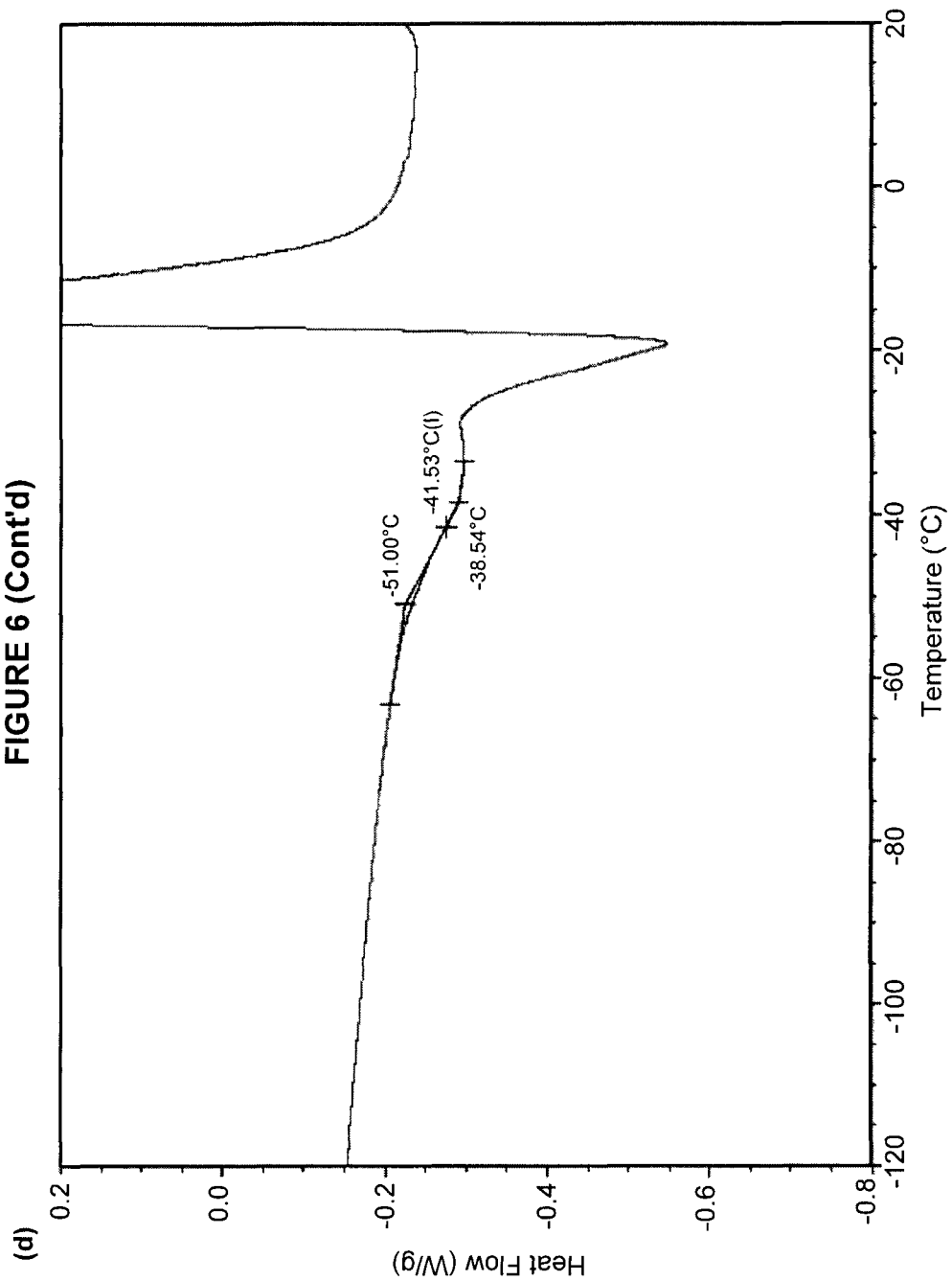
Figure 7:
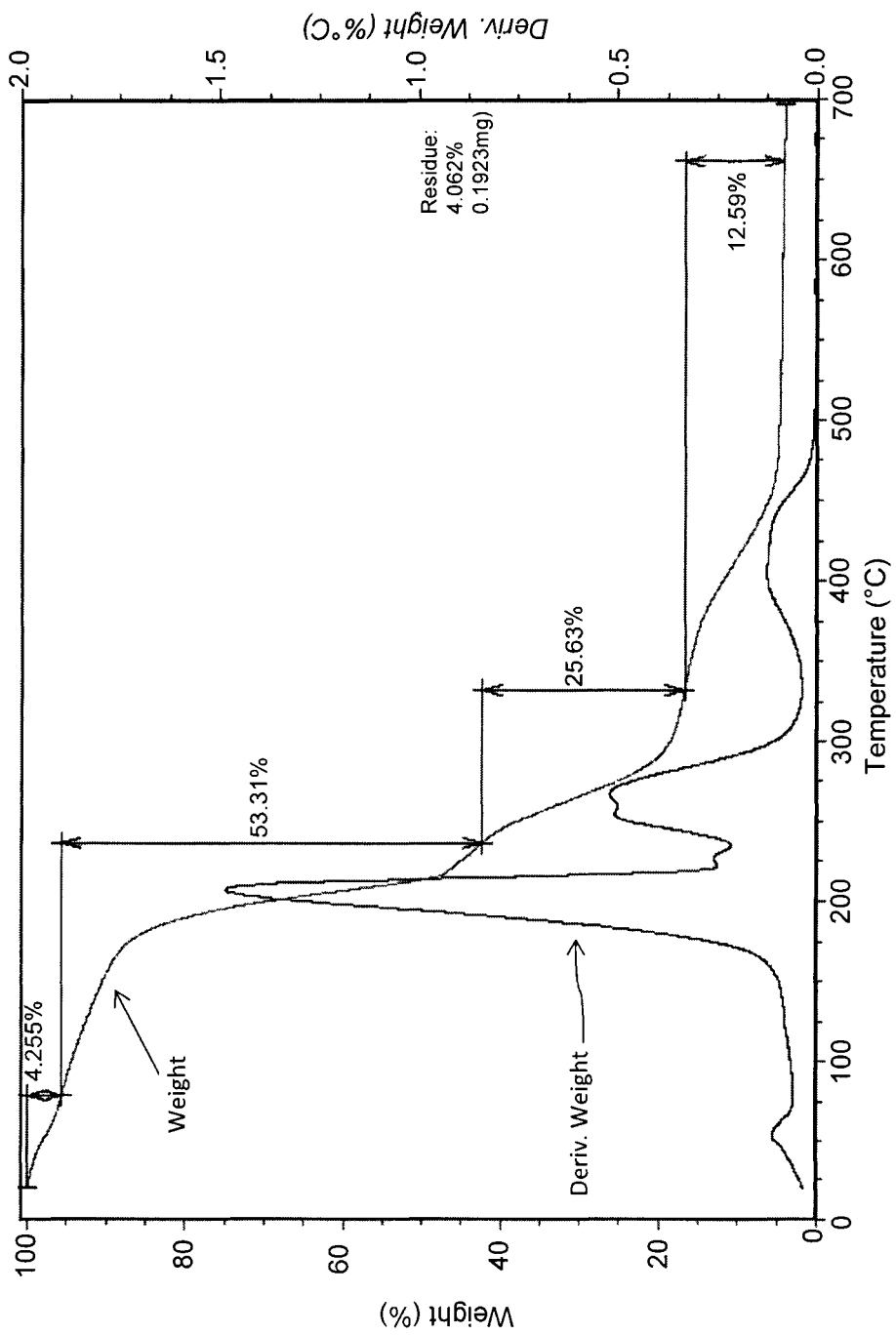
FIG. 7 is a TGA trace of a polymer of the disclosure under an $N_2$ atmosphere.
Figure 8:
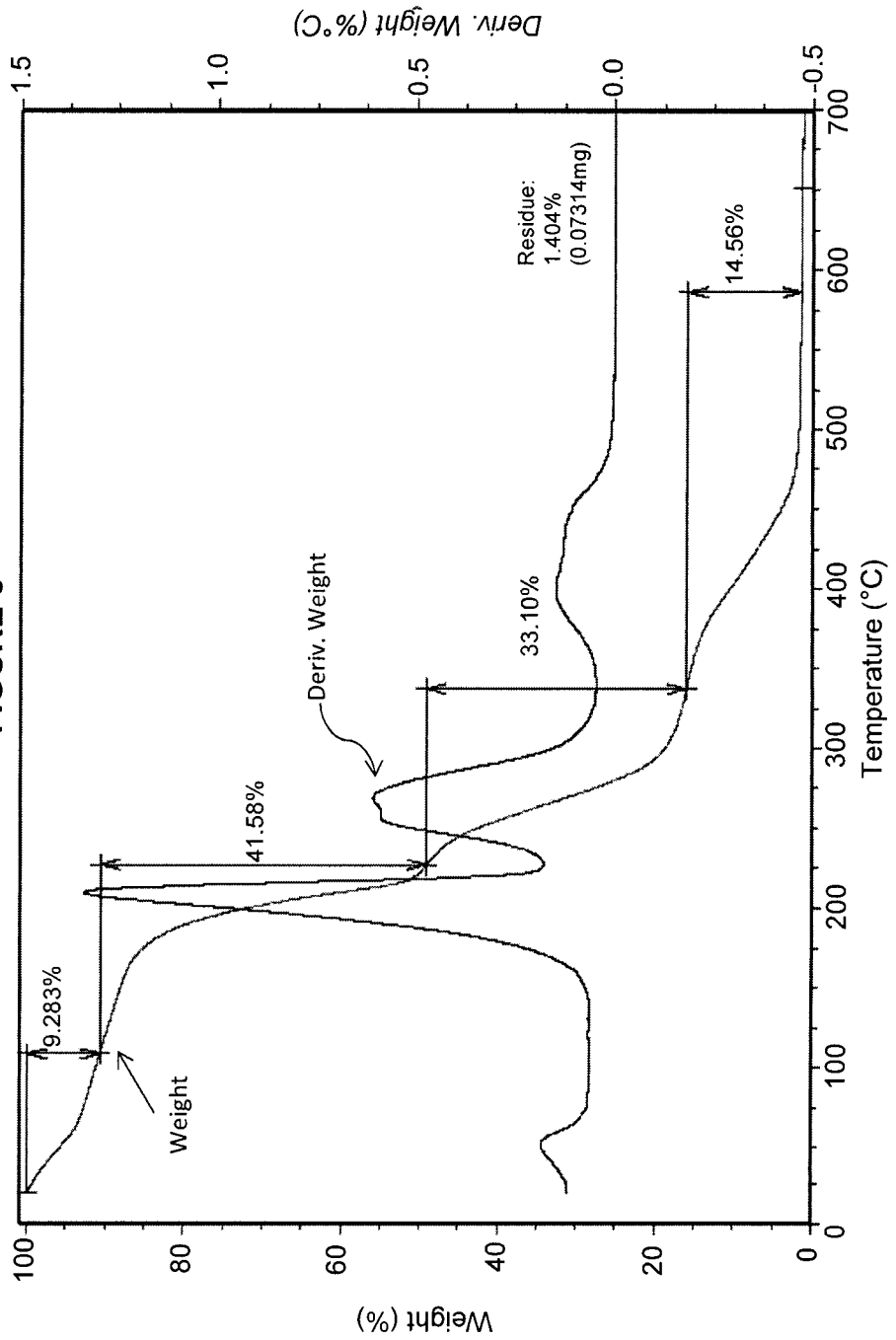
FIG. 8 is a TGA trace of a second polymer of the disclosure under an $N_2$ atmosphere.

The polymer was synthesized using a 1:1 mole ratio of the monomers [2-(Acryloyloxy)ethyl]trimethylammonium chloride solution (80% solution in water from Sigma Aldrich, AETA) and Benzalkonium chloride (Sigma Aldrich, BAC) using a 1% weight azo free radical initiator, according to known free radical polymerization methods that are known to one skilled in the art using a solvent free method. This polymer was characterized by Fourier Transform Infra-Red Spectroscopy (FIG. 1) and Proton and Carbon Nuclear Magnetic Resonance Spectroscopy (FIGS. 3, 4 respectively). This polymer sample will be referred to as Polymer 1.

Example 2

Preparation of Multi-Purpose Antimicrobial Polymer with Crosslinking Monomer

Figure 2:
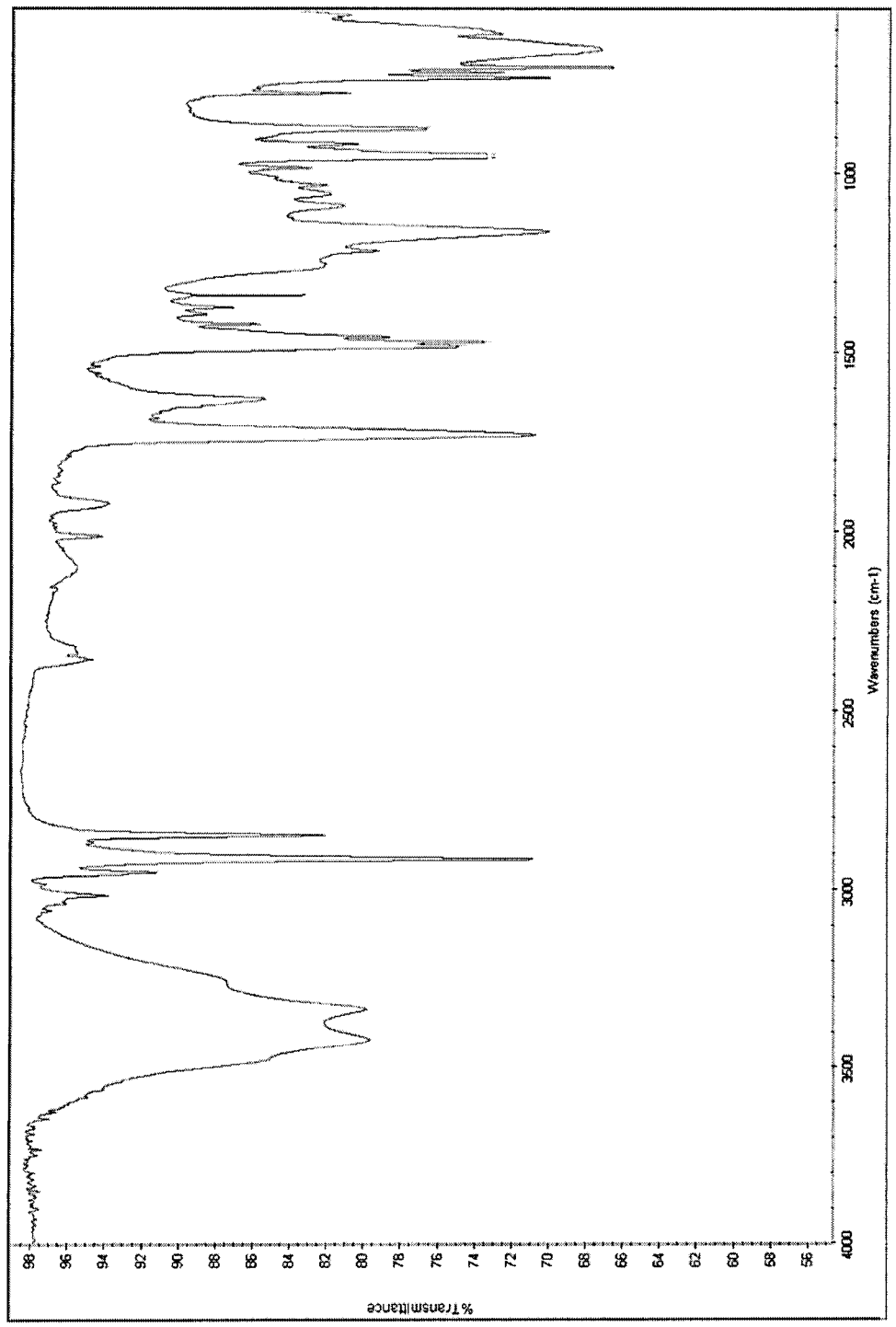
FIG. 2 is a Fourier Transform Infra-Red (FTIR) of a second polymer of the disclosure.

The polymer was synthesized using a 1:1 mole ratio of reactants described in Example 1 with the addition of 0.2 weight % (with respect to total monomer weight) crosslinking monomer pentaerythritol allyl ether (Sigma Aldrich 70%, APE) to the reaction mixture before initiating polymerization. The FTIR spectrum of the resulting polymer is presented in FIG. 2. This polymer sample will be referred to as Polymer 2.

Example 2A

Preparation of Multi-Purpose Antimicrobial Polymer with Plant Extract

This polymer was synthesized using a 15:10 mass ratio of reactants described in Example 1 with the addition of 0.1 g extract from sorbus decora before polymerization. The extraction can be done with any of the following methods: 1) cold extraction using different organic solvents with low vapour pressure followed by evaporation of solvent under vacuum, 2) extraction with water by evaporation of water under high vacuum, 3) supercritical fluid extraction.

Example 3

Preparation of an Antimicrobial Hydrogel Using the Crosslinking Monomer Pentaerythritol Allyl Ether The polymer was synthesized using a 1:1 mole ratio of reactants described in Example 1 with the addition of 5 weight % (with respect to total monomer weight) pentaerythritol allyl ether to the reaction before initiating polymerization. This polymer sample will be referred to as Polymer 3. This polymer acts as a hydrogel and swells when put in solution. 0.30 g of Polymer 3 was added to a 20 mL vial filled with distilled water. After 24 hours, the polymer was removed from solution and weighed 3.72 g, absorbing 1,140% of its own weight in water.

Example 4

Preparation of an Antimicrobial Hydrogel Using the Crosslinking Monomer N-methylene-bis-acrylamide The polymer was synthesized using a 1:1 mole ratio of reactants described in example 1 with the addition of 0.2 weight % (with respect to total monomer weight) 2-methylene-bis-acrylamide to the reaction before initiating polymerization. This polymer will be referred to as Polymer 4.

Another polymer was synthesized using a 1:3 mol ratio of BAC:AETA and 0.5 weight % (with respect to total monomer weight) 2-methylene-bis-acrylamide. A 24 hr swell test by immersing 0.1 g of the polymer in distilled water showed the mass swelling to 1.99 g when weighted after removing from water. The polymer absorbed water and grows approx. 20× or 2000% its initial mass in water.

Example 5

Preparations of the Compositions Containing AETA-homopolymer and BAC

Compositions containing various weight % (with respect to the mass of water) of the homopolymers of AETA (synthesized by well-known polymerization techniques known in the literature, referred to as hp-AETA), and benzalkonium chloride (BAC) were also prepared, by mixing and stirring the appropriate weight of polymer and benzalkonium chloride into solutions of water until they dissolved. For example a 2 wt. % of the composition solution consisting of 1% wt. of BAC and 1 wt % of hp-AETA was prepared by combining 0.5 g of BAC and 0.5 g of hp-AETA in 50 ml of water was prepared and labelled Composition-A. Similarly, a 1 wt % composition solution was prepared by combining 0.5 wt. % each of BAC and hp-AETA is labelled Composition-B. Additionally, a 1 wt. % composition consisting of 0.33% (0.15 g) hp-AETA and 0.66% (0.3 g) BAC in 45 ml water was also prepared and labelled Composition-C.

Example 6

Preparation of an Antimicrobial Liquid Copolymer Polymerized Via Free Radical Polymerization in the Presence of an Acid The polymer was synthesized using a 1:1 mole ratio of reactants described in example 1 with the addition of 10% weight hydrochloric acid (10% volume in water) with respect to total monomer weight. 1% weight azo free radical initiator was added in the reaction over a time interval of one hour.

Example 7

Viscosity Measurements

Viscosity measurements of a 1% weight solution in distilled water of Polymer 1 and Polymer 2 at pH 7 and 25° C. were taken using a Brookfield Synchrolectric viscometer model LVF. The values in centi-poise (mPa·s, m=milli) were calculated as per the specifications set out by the instrument manufacturer. The viscosity of the uncrosslinked Polymer 1 is 21 mPa·s, and the crosslinked Polymer 2 is 57.5 mPa·s respectively.

The viscosity of the compositions described in Example 5, were also similarly measured, as well as 1% wt. solutions of pure BAC and hp-AETA. The viscosity of 1 wt. % BAC was measured as 3.1 mPa·s, a 1 wt. % of CH12 was measured as 28.8 mPa·s. The viscosities of solutions containing Compositions A, B and C are 19.5 mPa·s, 10.7 mPa·s, and 7 mPa·s respectively.

On a purely mass equivalent basis, in comparison to Polymer 1, 1 g of Polymer 1 would contain approximately just under 2 parts by mass BAC to 1 part AETA (for a 1:1 mol equivalence), thus 1 g of Polymer 1 polymer should contain the same mass components as Comp C. The large difference in viscosity between 1% solutions of Composition-C and Polymer 1, indicates the formation of a copolymer between the BAC and AETA monomers. From a viscosity perspective, compositions of CH12 and BAC, require twice the mass (1% of each) to achieve similar rheological properties as a 1% wt. of the CH4 polymer.

Example 8

Anti-Microbial Activity

Antibacterial Susceptibility Testing Protocol

Compounds were tested for antibacterial activity, as described in Ma et al. (2011), against pure cultures of *Escherichia coli, Pseudomonas aeruginosa, Bacillus cereus, Proteus mirabilis/hauseri*, and *Staphylococcus aureus*, supplied by Ward's Natural Science Ltd. (St. Catherines, Ontario, Canada). All cultures were maintained on Tryptic Soy agar. These cultures were then transferred using an inoculation loop to 10 mL of Tryptic soy broth, and grown at 37° C. for 24 hours. Triplicates of plate and broth cultures were made in case of error or contamination.

Using a sterile swab, and aseptic techniques, the bacterial broth inocula were transferred to Mueller-Hinton plates and spread evenly, ensuring that the entire surface was inoculated. They were then left to dry for 3-5 minutes.

The following control discs were used: Penicillin (10 µg), Tetracycline (30 µg), Chloramphenicol (30 µg), and Ampicillin (10 µg). Four antibiotic discs containing different compounds were placed equidistant from each other on a Mueller-Hinton plate. Each compound had three replicates per species.

Plates were incubated for 18-24 hrs at 37° C., and then observed for rings of inhibition. If clear rings of inhibition were present, the diameter was measured twice using a caliper. Absence of rings of inhibition indicated a failed test, meaning the compound does not show enough antibacterial activity to be used in further testing.

Preparation of Novel Compound Discs

Each polymer was applied to sterile filter paper discs as a solution (15 mg of compound in 3 mL of solvent). Each disc received 20 µL of solution, and was allowed to dry, giving a final concentration of 100 µg of compound per disc.

Protocol for Antimicrobial Susceptibility Testing on Filamentous Fungi and Yeasts Adapted from Messer et al., (2007), this protocol was used to test novel compounds for antifungal properties against yeasts and fungi. Compounds were tested for antifungal activity against pure cultures of *Saccharomyces cerevisiae, Candida albicans* supplied by Ward's Natural Science Ltd. and *Aspergillus niger* and *Aspergillus fumigatus* supplied by Alere Inc. (Inverness Medical, Ottawa, Ontario, Canada). All cultures were maintained on Sabouraud agar. The cultures of *S. cerevisiae*, and *C. albicans* were transferred, using an inoculation loop, to Erlenmeyer flasks containing 100 mL of Malt Yeast Extract Broth, and grown with shaking at 15° C. for 48 hrs. The cultures of *A. niger* and *A. fumigatus* were transferred, using an inoculation loop, to new Sabouraud agar and grown for 48 hrs. at 27° C., and 35° C. respectively, to cause sporulation. Triplicates of all the plates and broth cultures were made in case of error or contamination.

Using a sterile swab, and aseptic techniques, the cell suspension of *S. cerevisiae*, and *C. albicans* were transferred to Sabouraud agar plates and spread evenly, ensuring that the entire surface was inoculated. They were then left to dry for 10 minutes. From the plates containing *A. niger* and *A. fumigatus* two small circles containing fungal growth of the *A Niger* or *A Fumigatus* fungi were cut from the agar plates, and using a glass/PTFE tissue homogenizer, were mixed and homogenized with 5 ml of sterile MilliQ water to create a suspension of fungal spores. Using a sterile swab, and aseptic techniques, the spore inocula of *A. niger* and *A. fumigatus* were transferred to Sabouraud agar plates and spread evenly, ensuring that the entire surface was inoculated. They were then left to dry for 10 minutes.

Amphotericin B (20 µg) premade discs were used as a control. Three antibiotic discs containing different compounds were place equidistant apart on each Sabouraud plate. Each compound had three replicates per species.

Plates containing *S. cerevisiae*, and *C. albicans* were incubated for 18-24 hrs at 37° C., *A. niger* for 48 hrs at room temperature, and *A. fumigatus* for 18-24 hrs at 35° C. After incubation, the plates were observed for rings of inhibition. If clear rings of inhibition were present, the diameter was measured twice using a caliper. Halos indicated partial inhibition of growth (Hicks et al., 2008). Absence of a ring of inhibition constitutes a failed test, meaning the compound did not show enough antifungal activity to be used in further testing.

The results of the anti-microbial and anti-fungal testing are shown in Tables 1 and 2 respectively. It demonstrates clearly that the anti-microbial action of the polymer is due to the incorporation of the BAC monomer into the polymer as a homopolymer of AETA shows no anti-microbial activity.

The results of the anti-microbial testing for an example of BAC-AETA-Plant extract (synthesized in Example 2A) are shown in Table 5. The anti-microbial action of the polymer is increased when the plant extract is included. The results show a synergistic effect of polymerization of plant extract with BAC and AETA.

Example 9 pH and Solubility of the Polymers

The compatibility of various solvents with Polymers 1 and 2 were tested by creating between 1 and 5% polymer (weight %) solutions in water, and various alcohols such as ethanol, indicating it is soluble in alcohol based solvents.

Further, a 1% weight solution in distilled water was prepared and the pH of solution adjusted using sodium hydroxide and hydrochloric acid to various values between 3 and 9 pH units. Over this range the polymers stayed in solution and the solution remained clear and stable.

Example 10

Compatibility of the Polymers with Other Chemicals in Formulations

The compatibility of various chemicals with Polymers 1 and 2 were tested by creating between 1 and 5% polymer (weight %) solutions in water. Different cationic, anionic, and zwitterionic surfactants commonly found in personal care product formulations were mixed into the Polymer 2 solutions.

A 1 weight % solution of Polymer 2 was mixed with the cationic surfactant, tetraoctylammonium bromide (0.3 g in 6 mL of $H_2O$+2 mL Polymer 2) and the pH stabilizer triethanolamine (0.2 mL+4 mL Polymer 2). When the tetraoctylammonium bromide solution was mixed an emulsion was formed and the solution remained stable when heated. Polymer 2 also remained stable in the triethanolamine mixture.

A 1 weight % solution of Polymer 2 was mixed with anionic base acetic acid (2 mL of 1M solution+2 mL Polymer 2), a polyanionic carbomer (0.1 mL of a 2 weight % solution+0.1 mL Polymer 2) and the anionic surfactant sodium lauryl sulfate (0.3 g in 3 mL+0.1 mL Polymer 2). The acetic acid was stable when mixed with Polymer 2, even when the pH was increased from 6 to 9 using sodium hydroxide. When Polymer 2 was added to the carbomer and sodium lauryl sulfate mixtures, an insoluble white precipitate immediately formed. The Polymer 2 solution was also compatible with the zwitterionic compound betaine (0.3 g in 3 mL $H_2O$+3 mL 1% Polymer 2).

A 1 weight % solution of Polymer 2 was mixed with two salts: 1M sodium chloride (3 mL+3 mL CH5) and magnesium sulfate (0.3 g in 6 mL $H_2O$+5 mL CH5). Both the sodium chloride and magnesium chloride remained stable and Polymer 2 is compatible with both.

Example 11

Hand Sanitizer Formulation

A hand sanitizer solution comprising a 1% weight solution of Polymer 2 in distilled water was prepared. This concentration is far in excess of the 100 µg concentration tested during the disk inhibition studies. The resulting solution was easy to use on the hands with the solution drying within approximately 30 s to 1 minute of application. The solution is also capable of being foamed, by pumping it through a foaming nozzle commercially available from foaming hand sanitizer liquid products and is capable of dispensing consistent foam.

Variations of the above sanitizer were also created wherein; scents and essential oils, as well as other ingredients such as aloe-vera for moisturizing were also added to the solution to create different types of aesthetically pleasing sanitizers. However, no additional rheological modifiers, emulsifiers or anti-microbial compounds were required to be added to the sanitizer due to the multifunctional nature of the polymer.

Example 12

Lotions and Sunscreens Formulated Using Polymers

Lotions, creams and sunscreens were formulated using Polymer 2. A summary of the formulations is provided in Table 3. The formulations were stored at room temperature, on the shelf for over 8 months and showed no discernable change in the organoleptic properties, or stability over that time frame.

Formulation 2A: comprising (all % are disclosed as weight % of the total formulation) 80.5% distilled water, 6% glycerol, 5% petroleum jelly, 4% cetearyl alcohol, 2% cucumber extract, 1% Polymer 2, and 0.25% dimethicone 500 was formulated by first dissolving Polymer 2 in water at 50° C. under stirring and then adding the glycerol, and cucumber extract to the aqueous solution. Separately the petroleum jelly, cetearyl alcohol and dimethicone were mixed at 50° C. under stirring to form a homogenous solution. The two solutions were then combined under magnetic stirring for 10 minutes before being allowed to cool to room temperature.

The activity of Formulation 2A is shown in Tables 1 and 2 and clearly demonstrates that the multi-functional polymer can be used to create cosmetic lotions that are also anti-microbial, and the polymer is not inactivated by incorporation into the formulation.

Cream 1: (all % are disclosed as weight % of the total formulation) comprising 79.75% distilled water, 5% cocoa butter, 5% cetearyl alcohol, 4% sorbitol, 3% aloe vera extract, 2% algae extract, 1% Polymer 2 and 0.25% dimethicone 500 was synthesized by first dissolving the Polymer 2 in water at 50° C., followed by the addition of sorbitol, aloe vera and algae extract to the solution under stirring. Separately the dimethicone, cetearyl alcohol and cocoa butter were mixed together under stirring at 50° C. to form a homogenous solution. The two solutions were then combined under magnetic stirring for 10 min before being allowed to cool to room temperature.

A sunscreen formulation comprising the ingredients and procedure of Cream 1 with the addition of 4% titanium dioxide (15 nm average particle size) (water content was reduced by 4 wt %) was formulated. The titanium dioxide is added to the cetaeryl alcohol solution before mixing of the two solutions.

Example 13

Modified ASTM E2276 Testing on Various % wt. Solutions of the Polymers as Hand Sanitizers Antimicrobial Sanitizer Testing—Polymer 1

Solutions of Polymer 1 were exposed to cultures of bacteria using a modification of ASTM E2276, a standard test method of for determining the bacteria-eliminating effectiveness of hygienic handwash agents. Synthetic vitro-skin® pads inoculated with the pathogenic microbes were exposed for 15 s to a polymer solution followed by recovery of the surviving organisms to determine the antimicrobial effectiveness of three wt. % solutions of Polymer 1 in water (Table 4). No bacteria were recovered from all of the test pads exposed to the 1% solution of Polymer 1, resulting in a reduction value of ≥5.14 $\log_{10}$, ≥6.54 $\log_{10}$, and ≥5.76 $\log_{10}$ for C. albicans, E. coli, and S. aureus, respectively, and demonstrating a very high antimicrobial effectiveness of the polymer solution.

Antimicrobial Sanitizer Testing—Polymer 2

Three solutions of Polymer 2 (0.5, 1 and 2% by weight of polymer in distilled water) were tested as potential hand sanitizing solutions based on a modified ASTM E 2276 (ASTM E2276-10, Standard Test Method for Determining the Bacteria-Eliminating Effectiveness of Hygienic Handwash and Handrub Agents Using the Fingerpads of Adults. West Conshohocken, Pa.: 2010) method where a 1 cm by 1 cm square of hydrated vitro-skin® was used in lieu of the finger pads of adult test subjects, as the test substrate. The vitroskin® by IMS Inc. was hydrated for 16-24 h prior to use as per manufacturer's instructions using a hydration chamber with a solution containing 85% water and 15% glycerin.

Briefly, the hydrated vitro-skin® test pads were inoculated with 10 µL of a 24 h bacterial (E. coli or S. aureus at 37° C.) or fungal (C. Alibicans at 35° C.) suspension and left until it was visibly dry (20-30 min). The test pads were then eluted (dry control), or exposed to a hard water (standard hardwater as prepared in accordance with AOAC 960.09 E and F (Official Methods of Analysis of AOAC INTERNATIONAL (2012) 19th Ed., AOAC INTERNATIONAL, Gaithersburg, Md., USA, Official Method 960.09. n.d.) to a standard hardness of 200 ppm) or a test solution, by placing 1 ml of the hard water, or test solution in a plastic vial and inverting the vial to cover the entire contaminated test pad. The liquid was allowed to maintain contact with the contaminated area for 10 to 15 s while subjecting the vial to 10 full inversions. Finally the test pad was scraped against the inside of the vial to recover as much fluid as possible and simulate the friction in hand antisepsis. The test pads were then immediately eluted.

Microbial elution of the test pads was performed by placing the contaminated pads over the mouth of a plastic vial containing 1 mL of the eluent. The vial was then inverted with the pad covering the vial mouth, and allowing the eluent to remain in contact with the test pad for 5-10 s followed by the inversion of the vial 20 times with the test pad covering the vial mouth. The entire procedure is repeated once more, and the vial turned upright, and the pad scraped across the inside of the vial to recover as much fluid as possible. For the test samples, a neutralizer solution containing (1.5% lecithin, 5% polysorbate 80, and 0.5% Sodium dodecyl sulfate prepared in phosphate buffered saline was used, while all other elution's were performed using normal saline (0.85% NaCl, pH 7.2-7.4). In the case of the inoculum control, the sample is eluted immediately after addition of the 10 µL microbial broth onto the test pad, while the dry control is eluted after 20-30 min drying of the microbial broth on the test pad.

The eluates were then diluted and plated in duplicate for E. coli and C. albicans and once for S. Aureus at the tested dilutions, to determine the CFU present in the eluates. Colonies of the test microorganisms were counted after 24 h incubation at 37±2° C. for the bacteria and 35±2° C. for C. albicans. In total, for each test organism four replicates of the hard water, test solutions, inoculum and drying controls were performed.

Neutralizer Validation

The neutralizer solution was validated under test conditions for all organisms based on ASTM E 1054 (ASTM E1054-08(2013), Standard Test Methods for Evaluation of Inactivators of Antimicrobial Agents. West Conshohocken, Pa.: n.d. doi:10.1520/E1054-08R13) using the above test conditions prior to the tests. Briefly, test pads were inoculated and left to dry as per the test conditions. Four tests, in three replicates were performed; in the first test (A) 0.1 ml of 2% sanitizer solution was added to 1 ml of the neutralizer buffer and immediately used to elute a contaminated test pad. In the second test (B), 1 ml of neutralizer buffer was use to elute a contaminated test pad, and in the third control test (C), 1 ml of sterile phosphate buffered saline was used to elute a contaminated test pad. In the fourth test (D), 1 ml of 2% sanitizer solution was used to elute a contaminated test pad. The samples were diluted and plated within 1 min of elution and after 1 h as the longest hold time, and incubated for 24 h after which the colonies on the plate counted to determine the CFU present in the eluates. The validity of the test was confirmed by statistical comparison of the number of survivors ($\text{Log}_{10}$) in tests A, B, and D to the control test C. Neutralization was considered adequate if the test A survivors is not statistically different from the test C survivors and if the test D survivors is statistically less than test C. The neutralizer is considered non-toxic if the test B recovery population is not statistically different from test C. The neutralizer used in the antimicrobial sanitizer tests showed no statistical difference between tests A, B and C, with the test D survivors statistically less than test C.

TABLE 1

Antibacterial Testing Results of the Various Polymers

| Compounds | Gram+ | | Gram− | | |
|---|---|---|---|---|---|
| | B. cereus | S. aureus | E. coli | P. hauseri | P. aeruginosa |
| Polymer 1 | 9.4 | 10.8 | 8.4 | 10.2 | 8.6 |
| Polymer 2 | 9.5 | 10.8 | 8.8 | 10.1 | 8.7 |
| AETA-BAC copolymer with a (3:1 mol ratio of AETA to BAC) | 9.9 | 11.8 | 8.4 | 10.1 | 12.3 |
| AETA homopolymer | NI | NI | NI | NI | NI |
| AETA monomer | NI | NI | NI | NI | NI |
| Formulation 2A | 8.7 | 9.8 | 9.2 | 8.3 | 7.6 |
| Ampicillin (10 µg) | 13.5 | 40.4 | 15.0 | 11 | 10.2 |
| Penicillin (10 µg) | NI | 43.8 | 19.5 | 19 | 7.0 |
| Chloramphenicol (30 µg) | 26.3 | 24.1 | 19.4 | 14.4 | 21.5 |
| Tetracycline (30 µg) | 20.3 | 24.7 | 20.4 | 13.7 | 9.9 |

NI means No Inhibition

TABLE 2

Antifungal Testing Results of the Various Polymers, NI, or — mean no Inhibition

| Compounds | Yeast | | Filamentous Fungi | |
|---|---|---|---|---|
| | C. albicans | S. cerevisiae | A. niger | A. fumigatus |
| Polymer 1 | 8.3 | 8.7 | NI | 9.0 |
| Polymer 2 | NI | 8.3 | NI | 7.9 |
| AETA-BAC copolymer with a (3:1 mol ratio of AETA to BAC) | NI | 8.4 | NI | 7.9 |
| AETA homopolymer | NI | NI | NI | NI |
| AETA monomer | NI | NI | NI | NI |
| Formulation 2A | 7.5 | 9.0 | NI | 7.9 |
| Amphotericin B (20 ug) | 13.6 | 8.39 | 15.5 | 12.5 |

NI means No Inhibition

TABLE 3

Composition of Formulations containing Polymer 2.

| Compounds | Lotion 1A | Lotion 1B | Lotion 1C | Lotion 2A | Lotion 2B | Lotion 2C | Lotion 2D | Lotion 3A | Sunscreen 1A | Sunscreen 1B | Sunscreen 1C |
|---|---|---|---|---|---|---|---|---|---|---|---|
| Polymer 2 | 1% | 1% | 1% | 1% | 1% | 1% | 1% | 1% | 1% | 1% | 1% |
| $H_2O$ | 81% | 80% | 81% | 86% | 80.5% | 82.75% | 78.5% | 80% | 68% | 70.75% | 77.5% |
| Sorbitol | 4% | 4% | 4% | — | — | — | — | — | — | 4% | 4% |
| Algae Extract | 1% | 1% | 2% | — | — | — | — | 5% | — | — | 2% |
| *Aloe Vera* | 1% | 3% | 3% | — | — | — | — | — | 6% | 4% | 3% |
| Cocoa Butter | 8% | 5% | 5% | — | — | — | — | — | — | — | 5% |
| Cetearyl alcohol | 4% | 4% | 3% | 4% | 4% | 4% | 4% | 5% | 4% | 4% | 3% |
| Dimethicone | — | 2% | 1% | 2% | 0.5% | 0.25% | 0.5% | — | — | 0.25% | 0.5% |
| Cucumber Fruit Extract | — | — | — | 2% | 2% | — | — | — | — | 2% | — |
| Petroleum Jelly | — | — | — | 5% | 5% | 3% | 3% | — | — | 10% | — |
| Glycerol | — | — | — | — | 6% | 5% | 7% | — | 2% | — | — |
| Stearic Acid | — | — | — | — | — | 4% | 4% | — | — | — | — |
| Coconut Oil | — | — | — | — | — | — | — | — | 4% | 7% | — |
| Almond Oil | — | — | — | — | — | — | — | 5% | 7% | — | — |
| Arabic gum | — | — | — | — | — | — | 2% | — | — | — | — |
| $TiO_2$ | — | — | — | — | — | — | — | — | 5% | 4% | 4% |

TABLE 4

Antimicrobial sanitizer testing using modified ASTM E2276 test method

| | C. albicans | | E. coli | | S. aureus | |
|---|---|---|---|---|---|---|
| Solution | % Reduction | Log Reduction | % Reduction | Log Reduction | % Reduction | Log Reduction |
| Hardwater | 99.36692 | 2.20 | 99.37681 | 2.20 | 99.47826 | 2.28 |
| Polymer 2 (2%) | 99.99905 | 5.02 | 100.0000 | 6.54 | 99.99913 | 5.06 |
| Polymer 2 (1%) | 100.00000 | 5.12 | 100.00000 | 6.54 | 100.00000 | 5.76 |
| Polymer 2 (0.5%) | 99.99905 | 5.02 | 99.99982 | 5.74 | 99.99739 | 4.58 |

TABLE 5

Antibacterial Testing Results of the Various Polymers (all 10 μg)

| | E. coli |
|---|---|
| AETA-BAC-*sorbus decora* copolymer with a (1:1.5:0.01 g ratio) | 9.9. |
| AETA-BAC polymer with a (1:1.5 g ratio) | 8.3 |
| AETA monomer | NI |
| *sorbus decora* extract | 0.5 |
| Ampicillin | 15.4 |
| Penicillin | 19.5 |
| Chloramphenicol | 17.4 |
| Tetracycline | 25.3 |

NI means No Inhibition

The invention claimed is:

1. A multi-functional anti-microbial polymer having the following structure

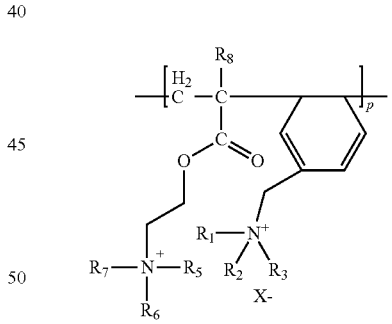

wherein $R_1$, $R_2$ and $R_3$ are independently or simultaneously optionally substituted H, $(C_1\text{-}C_{24})$-alkyl, $(C_2\text{-}C_{24})$-alkenyl, $(C_2\text{-}C_{24})$-alkynyl, $(C_6\text{-}C_{14})$-aryl, $(C_5\text{-}C_{14})$-heteroaryl or $(C_1\text{-}C_{10})$-alkylene-$(C_6\text{-}C_{14})$-aryl;

$R_5$, $R_6$ and $R_7$ are independently or simultaneously optionally substituted H, $(C_1\text{-}C_{24})$-alkyl, $(C_2\text{-}C_{24})$-alkenyl, or $(C_2\text{-}C_{24})$-alkynyl, $R_8$ is H or $(C_1\text{-}C_6)$-alkyl;

X is any suitable counter anion, and p is any integer between 1 and 1,000,000, wherein the polymer is not

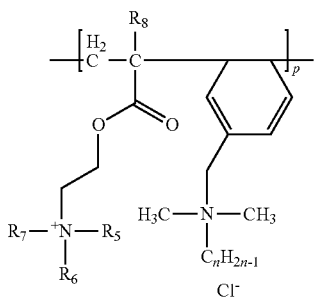

and n is 1, 8, 10, 12 14, 16 or 18.

2. The anti-microbial polymer claim 1, wherein the polymer is crosslinked with a suitable cross-linking agent.

3. The anti-microbial polymer of claim 2, wherein the suitable crosslinking agent is allylsucrose, pentaerythritol allyl ether, vinyl ether, dimethacrylate, di- or tri-vinylbenzene, alicyclic dienes, ethylene glycol dimethacrylate, polyethylene glycol dimethyacrylate, penta- and tetra-acrylates or N-methylene-bis-acrylamide.

4. The anti-microbial polymer of claim 1, wherein the polymer further comprises a monomer derived from a plant or fruit extract, wherein the monomer comprises a double bond or aromatic moiety.

5. The anti-microbial polymer of claim 4, wherein the plant or fruit extract comprises a tannin, terpernoid, alkaloid or combination thereof, wherein the tannin, terpenoid or alkaloid comprises a double bond or aromatic moiety which is incorporated into the polymer backbone.

6. The anti-microbial polymer of claim 5, wherein the plant or fruit extract is from sorbus decora, bistort plant or other plant comprising tannin, terpenoid, or alkaloid.

7. A hand sanitizing composition comprising a multifunctional anti-microbial polymer as defined in claim 1, and water.

8. A method for preparing a skin sanitizing composition, a disinfectant or cleansing composition, a hard surface cleaner, heavy duty cleaner or detergent composition or a personal care composition, comprising mixing a multifunctional anti-microbial polymer as claimed in claim 1, with at least one excipient selected from water, an emollient, an emulsifier, a fragrance, a humectant or moisturizer, pH adjuster, or a non-ionic or cationic surfactant.

9. The anti-microbial polymer of claim 1, wherein the polymer is incorporated into a hydrogel.

* * * * *